(12) United States Patent
Trieu et al.

(10) Patent No.: US 8,946,169 B2
(45) Date of Patent: *Feb. 3, 2015

(54) SPARC AND METHODS OF USE THEREOF

(71) Applicant: Abraxis BioScience, LLC, Los Angeles, CA (US)

(72) Inventors: Vuong Trieu, Agoura Hills, CA (US); Neil P. Desai, Los Angeles, CA (US); Patrick Soon-Shiong, Los Angeles, CA (US)

(73) Assignee: NantBioScience, Inc., Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/791,009

(22) Filed: Mar. 8, 2013

(65) Prior Publication Data

US 2013/0178422 A1    Jul. 11, 2013

Related U.S. Application Data

(63) Continuation of application No. 12/295,068, filed as application No. PCT/US2007/065486 on Mar. 29, 2007, now Pat. No. 8,415,304.

(60) Provisional application No. 60/788,208, filed on Mar. 31, 2006.

(51) Int. Cl.
| | | |
|---|---|---|
| *A01N 61/00* | (2006.01) | |
| *A61K 31/00* | (2006.01) | |
| *A61K 38/00* | (2006.01) | |
| *A61K 49/00* | (2006.01) | |
| *G01N 1/00* | (2006.01) | |
| *G01N 33/48* | (2006.01) | |
| *G01N 33/53* | (2006.01) | |
| *G01N 33/567* | (2006.01) | |
| *G01N 33/574* | (2006.01) | |
| *C12Q 1/00* | (2006.01) | |
| *A61K 47/48* | (2006.01) | |

(52) U.S. Cl.
CPC .... *A61K 47/48284* (2013.01); *G01N 33/57407* (2013.01); *G01N 33/57484* (2013.01); *G01N 2800/52* (2013.01)
USPC ................ 514/19.3; 424/9.1; 424/9.2; 435/4; 435/7.1; 435/7.21; 435/7.23; 436/63; 436/64; 436/174; 514/1; 514/1.1; 514/19.2

(58) Field of Classification Search
CPC .......... A61K 9/00; A61K 9/51; G01N 33/48; G01N 33/50; G01N 33/5005; G01N 33/574; G01N 33/57407
See application file for complete search history.

(56) References Cited

U.S. PATENT DOCUMENTS 8,415,304 B2 *   4/2013   Trieu et al. .................... 514/19.3
8,420,603 B2 *   4/2013   Trieu et al. .................... 514/19.3

* cited by examiner

*Primary Examiner* — Alana Harris Dent
(74) *Attorney, Agent, or Firm* — Leydig, Voit & Mayer, Ltd.

(57) ABSTRACT

The invention provides methods for predicting or determining the response of a mammalian tumor to a chemotherapeutic agent and for treating a mammalian tumor comprising detecting and quantifying the SPARC protein or RNA in a sample isolated from the mammal. The invention further provides kit for predicting the response of a mammalian tumor to a chemotherapeutic agent, comprising a means for the isolation of protein or RNA from the tumor, a SPARC protein or RNA detection and quantification means, control RNAs, and rules for predicting the response of the tumor based on the level of SPARC protein or RNA in tumor.

8 Claims, 16 Drawing Sheets

FIG. 1

SEQ ID NO: 1 -wild type SPARC amino acid sequence
(from Genbank NM_003118. [gi:48675809])

MRAWIFFLLCLAGRALAAPQQEALPDETEVVEETVAEVTEVSVG

ANPVQVEVGEFDDGAEETEEEVVAENPCQNHHCKHGKVCELDENNTPMCVCQDPTSCP

APIGEFEKVCSNDNKTFDSSCHFFATKCTLEGTKKGHKLHLDYIGPCKYIPPCLDSEL

TEFPLRMRDWLKNVLVTLYERDEDNNLLTEKQKLRVKKIHENEKRLEAGDHPVELLAR

DFEKNYNMYIFPVHWQFGQLDQHPIDGYLSHTELAPLRAPLIPMEHCTTRFFETCDLD

NDKYIALDEWAGCFGIKQKDIDKDLVI

FIG. 2

SEQ ID NO: 2 -WILD TYPE SPARC cDNA SEQUENCE

```
   1 gttgcctgtc tctaaacccc tccacattcc cgcggtcctt cagactgccc ggagagcgcg
  61 ctctgcctgc cgcctgcctg cctgccactg agggttccca gcaccatgag ggcctggatc
 121 ttctttctcc tttgcctggc cgggagggcc ttggcagccc ctcagcaaga agccctgcct
 181 gatgagacag aggtggtgga agaaactgtg gcagaggtga ctgaggtatc tgtgggagct
 241 aatcctgtcc aggtggaagt aggagaattt gatgatggtg cagaggaaac cgaagaggag
 301 gtggtggcgg aaaatccctg ccagaaccac cactgcaaac acggcaaggt gtgcgagctg
 361 gatgagaaca cacccccat gtgcgtgtgc caggacccca ccagctgccc agcccccatt
 421 ggcgagtttg agaaggtgtg cagcaatgac aacaagacct tgactcttc ctgccacttc
 481 tttgccacaa agtgcaccct ggagggcacc aagaagggcc acaagctcca cctggactac
 541 atcgggcctt gcaaatacat cccccttgc ctggactctg agctgaccga attcccctg
 601 cgcatgcggg actggctcaa gaacgtcctg gtcaccctgt atgagaggga tgaggacaac
 661 aaccttctga ctgagaagca gaagctgcgg gtgaagaaga tccatgagaa tgagaagcgc
 721 ctggaggcag gagaccaccc cgtggagctg ctgccccggg acttcgagaa gaactataac
 781 atgtacatct tccctgtaca ctgcagttc ggccagctgg accagcaccc cattgacggg
 841 tacctctccc acaccgagct ggctccactg cgtgctcccc tcatccccat ggagcattgc
 901 accacccgct ttttcgagac ctgtgacctg gacaatgaca agtacatcgc cctggatgag
 961 tgggccggct gcttcggcat caagcagaag gatatcgaca aggatcttgt gatctaaatc
1021 cactccttcc acagtaccgg attctctctt taaccctccc cttcgtgttt cccccaatgt
1081 ttaaaatgtt tggatggttt gttgttctgc ctggagacaa ggtgctaaca tagatttaag
1141 tgaatacatt aacggtgcta aaaatgaaaa ttctaaccca agacatgaca ttcttagctg
1201 taacttaact attaaggcct tttccacacg cattaatagt cccattttc tcttgccatt
1261 tgtagcttg cccattgtct tattggcaca tgggtggaca cggatctgct gggctctgcc
1321 ttaaacacac attgcagctt caactttct ctttagtgtt ctgtttgaaa ctaatactta
1381 ccgagtcaga ctttgtgttc atttcatttc agggtcttgg ctgcctgtgg gcttccccag
1441 gtggcctgga ggtgggcaaa gggaagtaac agacacacga tgttgtcaag gatggttttg
1501 ggactagagg ctcagtggtg ggagagatcc ctgcagaacc caccaaccag aacgtggttt
1561 gcctgaggct gtaactgaga gaaagattct ggggctgtgt tatgaaaata tagacattct
1621 cacataagcc cagttcatca ccatttcctc ctttacctt cagtgcagtt tcttttcaca
1681 ttaggctgtt ggttcaaact tttgggagca cggactgtca gttctctggg aagtggtcag
1741 cgcatcctgc agggcttctc ctcctctgtc ttttggagaa ccagggctct tctcagggc
1801 tctagggact gccaggctgt ttcagccagg aaggccaaaa tcaagagtga gatgtagaaa
1861 gttgtaaaat agaaaagtg gagttggtga atcggttgtt cttcctcac atttggatga
1921 ttgtcataag gttttagca tgttcctcct ttcttcacc ctccctttt tcttctatt
1981 aatcaagaga aacttcaaag ttaatgggat ggtcggatct cacaggctga gaactcgttc
2041 acctccaagc atttcatgaa aaagctgctt cttattaatc atacaaactc tcaccatgat
2101 gtgaagagtt tcacaaatcc ttcaaaataa aagtaatga cttagaaact gccttcctgg
2161 gtgatttgca tgtgtcttag tcttagtcac cttattatcc tgacacaaaa acacatgagc
2221 atacatgtct acacatgact acacaaatgc aaacctttgc aaacacatta tgcttttgca
2281 cacacacacc tgtacacaca caccggcatg tttatacaca gggagtgtat ggttcctgta
2341 agcactaagt tagctgtttt catttaatga cctgtggttt aacccttttg atcactacca
2401 ccattatcag caccagactg agcagctata tccttttatt aatcatggtc attcattcat
2461 tcattcattc acaaaatatt tatgatgtat ttactctgca ccaggtccca tgccaagcac
2521 tggggacaca gttatggcaa agtagacaaa gcatttgttc atttggagct tagagtccag
2581 gaggaataca ttagataatg acacaatcaa atataaattg caagatgtca caggtgtgat
2641 gaagggagag taggagagac catgagtatg tgtaacagga ggacacagca ttattctagt
2701 gctgtactgt tccgtacgga agccactacc cacatgtaac ttttaagat taaattaa
2761 attagttaac attcaaaacg cagctcccca atcacactag caacatttca agtgcttgag
2821 agccatgcat gattagtggt taccctattg aataggtcag aagtagaatc ttttcatcat
2881 cacagaaagt tctattggac agtgctcttc tagatcatca taagactaca gagcactttt
2941 caaagctcat gcatgttcat catgttagtg tcgtattttg agctggggtt ttgagactcc
3001 ccttagagat agagaaacag acccaagaaa tgtgctcaat tgcaatgggc cacataccta
3061 gatctccaga tgtcatttcc cctctcttat tttaagttat gttaagatta ctaaaacaat
3121 aaaagctcct aaaaaatcaa aaaaaaaaa aaaaaaaaa aaaaaaaaa aaaaaaa
```

FIG. 3
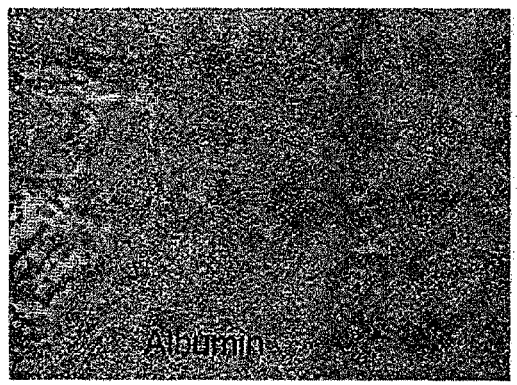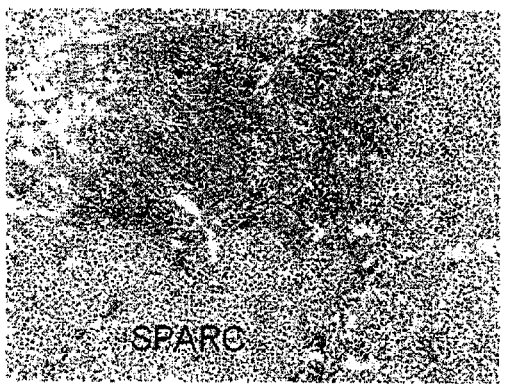

Transcytosis of Paclitaxel across Endothelial Cell Monolayers

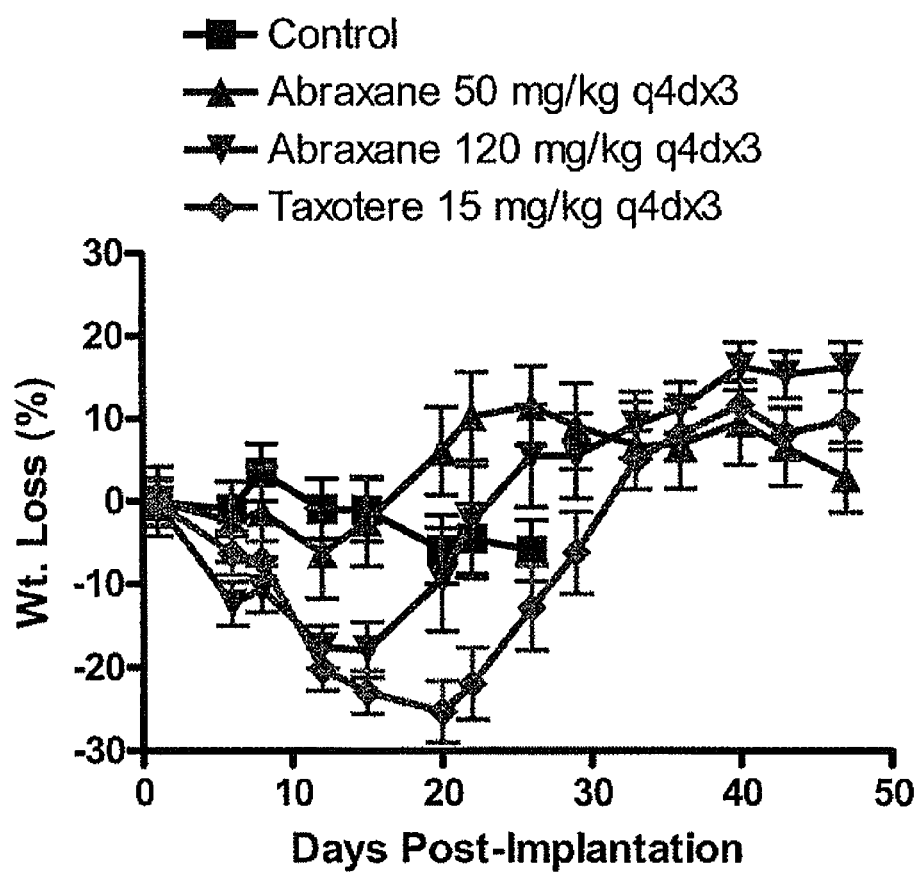

SEQUENCE LISTING

<160> NUMBER OF SEQ ID NOS: 2

<210> SEQ ID NO 1
<211> LENGTH: 303
<212> TYPE: PRT
<213> ORGANISM: Homo sapiens

<400> SEQUENCE: 1

```
Met Arg Ala Trp Ile Phe Phe Leu Leu Cys Leu Ala Gly Arg Ala Leu
1               5                   10                  15

Ala Ala Pro Gln Gln Glu Ala Leu Pro Asp Glu Thr Glu Val Val Glu
                20                  25                  30

Glu Thr Val Ala Glu Val Thr Glu Val Ser Val Gly Ala Asn Pro Val
                35                  40                  45

Gln Val Glu Val Gly Glu Phe Asp Asp Gly Ala Glu Glu Thr Glu Glu
        50                  55                  60

Glu Val Val Ala Glu Asn Pro Cys Gln Asn His His Cys Lys His Gly
65                  70                  75                  80

Lys Val Cys Glu Leu Asp Glu Asn Asn Thr Pro Met Cys Val Cys Gln
                85                  90                  95

Asp Pro Thr Ser Cys Pro Ala Pro Ile Gly Glu Phe Glu Lys Val Cys
                100                 105                 110

Ser Asn Asp Asn Lys Thr Phe Asp Ser Ser Cys His Phe Phe Ala Thr
            115                 120                 125

Lys Cys Thr Leu Glu Gly Thr Lys Lys Gly His Lys Leu His Leu Asp
        130                 135                 140

Tyr Ile Gly Pro Cys Lys Tyr Ile Pro Pro Cys Leu Asp Ser Glu Leu
145                 150                 155                 160

Thr Glu Phe Pro Leu Arg Met Arg Asp Trp Leu Lys Asn Val Leu Val
                165                 170                 175

Thr Leu Tyr Glu Arg Asp Glu Asp Asn Asn Leu Leu Thr Glu Lys Gln
            180                 185                 190

Lys Leu Arg Val Lys Lys Ile His Glu Asn Glu Lys Arg Leu Glu Ala
        195                 200                 205

Gly Asp His Pro Val Glu Leu Leu Ala Arg Asp Phe Glu Lys Asn Tyr
    210                 215                 220
```

Asn Met Tyr Ile Phe Pro Val His Trp Gln Phe Gly Gln Leu Asp Gln
225                 230                 235                 240

His Pro Ile Asp Gly Tyr Leu Ser His Thr Glu Leu Ala Pro Leu Arg
            245                 250                 255

Ala Pro Leu Ile Pro Met Glu His Cys Thr Thr Arg Phe Phe Glu Thr
            260                 265                 270

Cys Asp Leu Asp Asn Asp Lys Tyr Ile Ala Leu Asp Glu Trp Ala Gly
        275                 280                 285

Cys Phe Gly Ile Lys Gln Lys Asp Ile Asp Lys Asp Leu Val Ile
    290                 295                 300

<210> SEQ ID NO 2
<211> LENGTH: 3178
<212> TYPE: DNA
<213> ORGANISM: Homo sapiens

<400> SEQUENCE: 2

| | | | | | |
|---|---|---|---|---|---|
| gttgcctgtc | tctaaacccc | tccacattcc | cgcggtcctt | cagactgccc | ggagagcgcg | 60 |
| ctctgcctgc | cgcctgcctg | cctgccactg | agggttccca | gcaccatgag | ggcctggatc | 120 |
| ttctttctcc | tttgcctggc | cgggagggcc | ttggcagccc | ctcagcaaga | agccctgcct | 180 |
| gatgagacag | aggtggtgga | agaaactgtg | gcagaggtga | ctgaggtatc | tgtgggagct | 240 |
| aatcctgtcc | aggtggaagt | aggagaattt | gatgatggtg | cagaggaaac | cgaagaggag | 300 |
| gtggtggcgg | aaaatccctg | ccagaaccac | cactgcaaac | acggcaaggt | gtgcgagctg | 360 |
| gatgagaaca | caccccccat | gtgcgtgtgc | caggacccca | ccagctgccc | agcccccatt | 420 |
| ggcgagtttg | agaaggtgtg | cagcaatgac | aacaagacct | cgactcttc | ctgccacttc | 480 |
| tttgccacaa | agtgcaccct | ggagggcacc | aagaagggcc | acaagctcca | cctggactac | 540 |
| atcgggcctt | gcaaatacat | ccccccttgc | ctggactctg | agctgaccga | attccccctg | 600 |
| cgcatgcggg | actggctcaa | gaacgtcctg | gtcaccctgt | atgagaggga | tgaggacaac | 660 |
| aaccttctga | ctgagaagca | gaagctgcgg | gtgaagaaga | tccatgagaa | tgagaagcgc | 720 |
| ctggaggcag | agaccacccc | cgtgagctg | ctggcccggg | acttcgagaa | gaactataac | 780 |
| atgtacatct | tccctgtaca | ctggcagttc | ggccagctgg | accagcaccc | cattgacggg | 840 |
| tacctctccc | acaccgagct | ggctccactg | cgtgctcccc | tcatccccat | ggagcattgc | 900 |
| accacccgct | ttttcgagac | ctgtgacctg | gacaatgaca | agtacatcgc | cctggatgag | 960 |
| tgggccggct | gcttcggcat | caagcagaag | gatatcgaca | aggatcttgt | gatctaaatc | 1020 |
| cactccttcc | acagtaccgg | attctctctt | taaccctccc | cttcgtgttt | ccccaatgt | 1080 |
| ttaaaatgtt | tggatggttt | gttgttctgc | ctggagacaa | ggtgctaaca | tagatttaag | 1140 |
| tgaatacatt | aacggtgcta | aaaatgaaaa | ttctaaccca | agacatgaca | ttcttagctg | 1200 |
| taacttaact | attaaggcct | tttccacacg | cattaatagt | cccatttttc | tcttgccatt | 1260 |
| tgtagctttg | cccattgtct | tattggcaca | tgggtggaca | cggatctgct | gggctctgcc | 1320 |
| ttaaacacac | attgcagctt | caactttct | ctttagtgtt | ctgtttgaaa | ctaatactta | 1380 |
| ccgagtcaga | ctttgtgttc | atttcatttc | agggtcttgg | ctgcctgtgg | gcttccccag | 1440 |
| gtggcctgga | ggtgggcaaa | gggaagtaac | agacacacga | tgttgtcaag | gatggttttg | 1500 |
| ggactagagg | ctcagtggtg | ggagagatcc | ctgcagaacc | caccaaccag | aacgtggttt | 1560 |
| gcctgaggct | gtaactgaga | gaaagattct | gggctgtgt | tatgaaaata | tagacattct | 1620 |
| cacataagcc | cagttcatca | ccatttcctc | ctttaccttt | cagtgcagtt | tcttttcaca | 1680 |

```
                                                           -continued
ttaggctgtt ggttcaaact tttgggagca cggactgtca gttctctggg aagtggtcag    1740
cgcatcctgc agggcttctc ctcctctgtc ttttggagaa ccaggctct tctcaggggc     1800 tctagggact gccaggctgt ttcagccagg aaggccaaaa tcaagagtga gatgtagaaa   1860
gttgtaaaat agaaaaagtg gagttggtga atcggttgtt ctttcctcac atttggatga    1920
ttgtcataag gtttttagca tgttcctcct tttcttcacc ctcccctttt ttcttctatt     1980
aatcaagaga aacttcaaag ttaatgggat ggtcggatct cacaggctga gaactcgttc    2040
acctccaagc atttcatgaa aaagctgctt cttattaatc atacaaactc tcaccatgat   2100
gtgaagagtt tcacaaatcc ttcaaaataa aaagtaatga cttagaaact gccttcctgg   2160
gtgatttgca tgtgtcttag tcttagtcac cttattatcc tgacacaaaa acacatgagc   2220
atacatgtct acacatgact acacaaatgc aaacctttgc aaacacatta tgcttttgca   2280
cacacacacc tgtacacaca caccggcatg tttatacaca gggagtgtat ggttcctgta   2340
agcactaagt tagctgtttt catttaatga cctgtggttt aacccttttg atcactacca   2400
ccattatcag caccagactg agcagctata tccttttatt aatcatggtc attcattcat    2460
tcattcattc acaaaatatt tatgatgtat ttactctgca ccaggtccca tgccaagcac   2520
tggggacaca gttatggcaa agtagacaaa gcatttgttc atttggagct tagagtccag   2580
gaggaataca ttagataatg acacaatcaa atataaattg caagatgtca caggtgtgat   2640
gaagggagag taggagagac catgagtatg tgtaacagga ggacacagca ttattctagt   2700
gctgtactgt tccgtacggc agccactacc cacatgtaac ttttttaagat ttaaatttaa  2760 attagttaac attcaaaacg cagctcccca atcacactag caaacatttca agtgcttgag  2820 agccatgcat gattagtggt taccctattg aataggtcag aagtagaatc ttttcatcat   2880
cacagaaagt tctattggac agtgctcttc tagatcatca taagactaca gagcactttt   2940
caaagctcat gcatgttcat catgttagtg tcgtattttg agctggggtt ttgagactcc    3000
ccttagagat agagaaacag acccaagaaa tgtgctcaat tgcaatgggc cacataccta   3060
gatctccaga tgtcatttcc cctctcttat tttaagttat gttaagatta ctaaaacaat   3120
aaaagctcct aaaaaatcaa aaaaaaaaaa aaaaaaaaaa aaaaaaaaaa aaaaaaa      3178
```

SPARC AND METHODS OF USE THEREOF

CROSS-REFERENCE TO RELATED APPLICATIONS

This patent application is a continuation of copending U.S. patent application Ser. No. 12/295,068 filed Oct. 22, 2008, which is a national phase of International Patent Application no. PCT/US2007/065486, filed Mar. 29, 2007, which claims priority to U.S. Provisional Patent Application No. 60/788,208, filed Mar. 31, 2006, all of which are hereby incorporated by reference.

FIELD OF THE INVENTION

This invention relates to methods for treating cancer; as well as other diseases involving abnormal proliferative, hyperplastic, remodeling, inflammatory activity in tissues and organs.

BACKGROUND OF THE INVENTION

Albumin nanoparticle formulations have been shown to reduce toxicity of poorly soluble therapeutic agents. For example, U.S. Pat. No. 6,537,579 discloses an albumin-nanoparticle paclitaxel formulation which is free of toxic emulsifiers.

The anticancer agent paclitaxel, marketed under the trademark Taxol® by Bristol Myers Squibb, is currently approved for the treatment of several cancers including ovarian, lung, and breast cancer. The major limitation to the use of paclitaxel is its poor solubility. Consequently, the Taxol® formulation contains Cremophor® EL as the solubilizing vehicle, but the presence of Cremophor® in this formulation has been linked to severe hypersensitivity reactions in animals (Lorenz et al., Agents Actions 7, 63-67, 1987), and humans (Weiss et al., J. Clin. Oncol. 8, 1263-1268, 1990). Accordingly, patients receiving Taxol® require premedication with corticosteroids (dexamethasone) and antihistamines to reduce the hypersensitivity and anaphylaxis that occurs due to the presence of Cremophor®.

In contrast, Abraxane® also known as ABI-007 is a Cremophor®-free, albumin-nanoparticle formulation of paclitaxel, marketed by Abraxis Oncology. The use of an albumin nanoparticle as a vehicle results in the formation of a colloid when reconstituted with saline. Based on clinical studies, it has been shown that the use of Abraxane® is characterized by reduced hypersensitivity reactions as compared with Taxol®. Accordingly, premedication is not required for patients receiving Abraxane®.

Another advantage of the albumin-nanoparticle formulation is that by excluding toxic emulsifiers it is possible to administer higher doses of paclitaxel at more frequent intervals than is currently possible with Taxol®. The potential exists that enhanced efficacy could be seen in solid tumors as a consequence of (i) higher tolerable doses (300 mg/m$^2$), (ii) longer half-life, (iii) prolonged local tumor availability and/or (iv) sustained in vivo release. Abraxane® reduces hypersensitivity reactions while maintaining or improving the chemotherapeutic effect of the drug.

It is known that colloidal nanoparticles or particles <200 nm in size tend to concentrate at the tumor site due to leaky vasculatures. This effect has been described for several liposomal formulations (Papahadjopoulos, et al., Proc. Natl. Acad. Sci. U.S.A. 88, 11460, 1991); (Gabizon, A., Cancer Res., 52, 891, 1992); (Dvorak, et al., Am. J. Pathol. 133, 95, 1988); (Dunn, et al., Pharm, Res., 11, 1016-1022, 1994); and (Gref, et al, Science 263, 1600-1603, 1994). It is possible that localized nanoparticles of paclitaxel at the tumor site may result in slow release of the drug at the tumor site resulting in greater efficacy when compared to administration of the drug in its solubilized (Cremophor®-containing) form.

Such nanoparticle formulations comprise at least about 50% of the active agent in nanoparticle form. Further, such nanoparticle formulations comprise at least about 60%, at least about 70%, at least about 80%, or at least about 90% of the active agent in nanoparticle form. Moreover, such nanoparticle formulations comprise at least about 95% or at least about 98% of the active agent in nanoparticle form.

Secreted Protein, Acidic, Rich in Cysteines (SPARC), also known as osteonectin, is a 281 amino acid glycoprotein. SPARC has affinity for a wide variety of ligands including cations (e.g., $Ca^{2+}$, $Cu^{2+}$, $Fe^{2+}$), growth factors (e.g., platelet derived growth factor (PDGF), and vascular endothelial growth factor (VEGF)), extracellular matrix (ECM) proteins (e.g., collagen I-V and collagen IX, vitronectin, and thrombospondin-1), endothelial cells, platelets, albumin, and hydroxyapaptite. SPARC expression is developmentally regulated, and is predominantly expressed in tissues undergoing remodeling during normal development or in response to injury (see, e.g., Lane et al., FASEB J., 8, 163-173 (1994)). High levels of SPARC protein are expressed in developing bones and teeth.

SPARC is a matricellular protein upregulated in several aggressive cancers, but is absent in normal tissues (Porter et al., J. Histochem. Cytochem., 43, 791 (1995)). Indeed, SPARC expression is induced among a variety of tumors (e.g., bladder, liver, ovary, kidney, gut, and breast). In bladder cancer, for example, SPARC expression has been associated with advanced carcinoma. Invasive bladder tumors of stage T2 or greater have been shown to express higher levels of SPARC than bladder tumors of stage T1 (or less superficial tumors), and have poorer prognosis (see, e.g., Yamanaka et al., J. Urology, 166, 2495-2499 (2001)). In meningiomas, SPARC expression has been associated with invasive tumors only (see, e.g., Rempel et al., Clincal Cancer Res., 5, 237-241 (1999)). SPARC expression also has been detected in 74.5% of in situ invasive breast carcinoma lesions (see, e.g., Bellahcene, et al., Am. J. Pathol., 146, 95-100 (1995)), and 54.2% of infiltrating ductal carcinoma of the breast (see, e.g., Kim et al., Korean Med. Sci., 13, 652-657 (1998)). SPARC expression also has been associated with frequent microcalcification in breast cancer (see, e.g., Bellahcene et al., supra), suggesting that SPARC expression may be responsible for the affinity of breast metastases for the bone. SPARC is also known to bind albumin (see, e.g., Schnitzer, J. Biol. Chem., 269, 6072 (1994)).

Antibody therapy is an effective method for controlling disease wherein a specific protein marker can be identified. Examples include Avastin—an anti-VEGF antibody, Rituxan—an anti-CD20 antibody, and Remicade—an anti-TNF antibody. As such, an antibody against SPARC would represent an important therapeutic agent for treating human and other mammalian tumors, as well as other proliferative, hyperplastic, remodeling, and inflammatory disorders that express the SPARC protein. In addition, an antibody against SPARC conjugated with an imaging or contrast agent would be a means of detecting and diagnosing such disorders.

There remains a need for a method of treating human and other mammalian tumors, as well as other proliferative, hyperplastic, remodeling, and inflammatory disorders. Moreover, there remains a need for predicting or determining the response of a human or other mammalian tumor in order to predict or evaluate the effectiveness of the chemotherapeutic agent. In addition, suitable means are needed in order to detect and diagnose such disorders. These and other advantages of the invention, as well as additional inventive features, will be apparent from the description of the invention provided herein.

BRIEF SUMMARY OF THE INVENTION

The invention provides a method for predicting or determining the response of a mammalian tumor or other proliferative disease to a chemotherapeutic agent or other anticancer agent, wherein the method comprises the steps of (a) isolating a biological sample from the mammal, (b) detecting the expression of SPARC protein or RNA in the biological sample, and (c) quantifying the amount of SPARC protein in the biological sample. The invention provides for embodiments wherein the biological sample is isolated from the tumor (or tissue involved with a proliferative disease) or from a bodily fluid, such as, e.g., cerebrospinal fluid, blood, plasma, serum or urine.

In addition, the invention provides a method of treating a tumor or other proliferative disease in a mammal with a chemotherapeutic agent or other anticancer agent comprising (a) isolating a biological sample from the mammal, (b) detecting the expression of SPARC protein or RNA in the biological sample, (c) quantifying the amount of SPARC protein or RNA in the biological sample, (d) determining if the SPARC protein or RNA is present at a level indicating the use of the chemotherapeutic agent or other anticancer agent, and (e), if, based on the SPARC protein or RNA level, it is indicated, administering a therapeutically effective amount of the chemotherapeutic agent or other anticancer agent.

Further, the invention provides a kit for predicting the response of a mammalian tumor or other proliferative disease to a chemotherapeutic agent or other anticancer agent, comprising a means for the isolation of protein from the tumor, a SPARC protein detection and quantification means, control proteins, and rules for predicting the response of the tumor. The invention also provides for a kit for predicting the response of a mammalian tumor or other proliferative disease to a chemotherapeutic agent or other anticancer agent, comprising a means for the isolation of RNA from the tumor, a SPARC RNA detection and quantification means, control RNAs, and rules for predicting the response of the tumor based on the level of SPARC RNA in tumor.

The invention provides for a method for predicting or determining the response of a mammalian tumor to a chemotherapeutic agent, as well as a method of treating a mammalian tumor with a chemotherapeutic agent, wherein the chemotherapeutic agent is, e.g., docetaxel, paclitaxel, such as Abraxane®, or combinations thereof. The invention further provides for embodiments, wherein the prediction of the response of a mammalian tumor to a chemotherapeutic agent is positively or negatively correlated with SPARC levels.

The invention provides for a methods for predicting or determining the response of a mammalian tumor or treating a mammalian tumor with a chemotherapeutic agent, where including, for example without limitation, wherein the mammal is a human and the tumor is a carcinoma of the breast, ovary, head and neck, lung, colon, bladder or kidney.

The invention further provides a method for utilizing the albumin-binding protein as a therapeutic, for utilizing SPARC and antibodies against SPARC or SPARC binding-proteins as therapeutics, for delivering a chemotherapeutic agent to a disease site in a mammal, in which the method comprises administering to the mammal a therapeutically effective amount of a pharmaceutical composition, wherein the pharmaceutical composition comprises the chemotherapeutic agent coupled to a compound capable of binding an albumin-binding protein and a pharmaceutically acceptable carrier. In addition, the invention provides a composition comprising a chemotherapeutic agent coupled to a compound capable of binding a SPARC protein and a pharmaceutically acceptable carrier. Moreover, the invention provides a delivery agent comprising a SPARC recognition group and a therapeutic agent, wherein the therapeutic agent is coupled to the SPARC recognition group. Furthermore, the invention provides a method for delivering a chemotherapeutic agent to a tumor in a mammal, wherein the method comprises administering to a mammal a therapeutically effective amount of a pharmaceutical composition, wherein the pharmaceutical composition comprises a chemotherapeutic agent coupled to a SPARC protein capable of binding albumin and a pharmaceutically acceptable carrier. The invention compositions may be small molecule, large molecule or proteins.

BRIEF DESCRIPTION OF THE DRAWINGS

FIG. 1 depicts the human SPARC amino acid sequence (SEQ ID NO: 1).

FIG. 2 depicts the human SPARC cDNA sequence (SEQ ID NO: 2).

FIG. 3 illustrates albumin and SPARC staining in MX-1 tumor xenografts.

FIG. 9A-B illustrate the comparative efficacy (A, tumor volume) and toxicity (B, % weight loss) of Abraxane and Taxotere for the treatment of a PC3 xenograft.

DETAILED DESCRIPTION OF THE INVENTION

Figure 4:
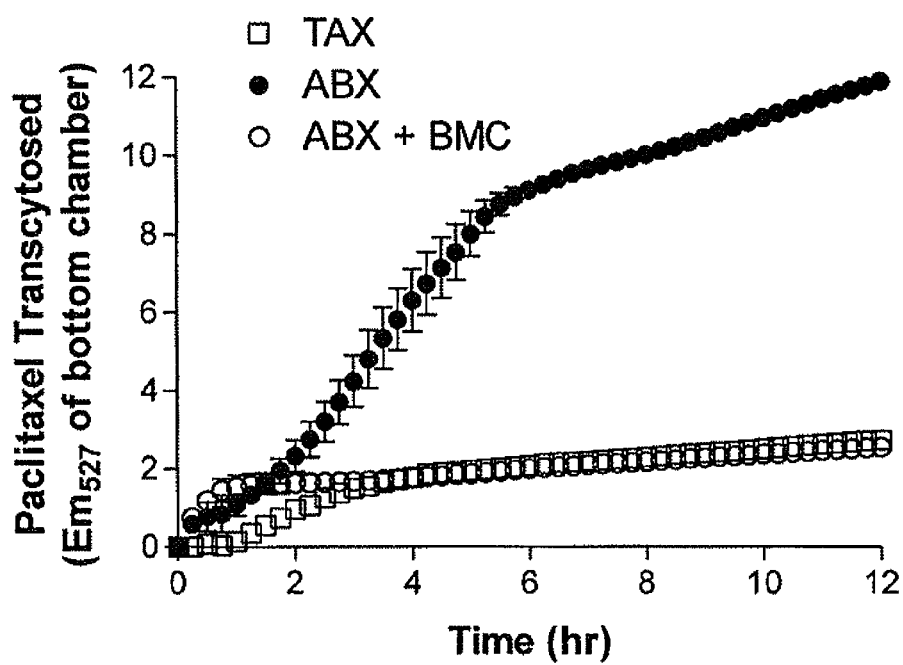
FIG. 4 illustrates transcytosis of paclitaxel across endothelial cell monolayers.

It has now been discovered that an additional mechanism of localization exists for compositions comprising albumin-binding proteins. Albumin-binding proteins, such as SPARC, cubilin, and TGFβ, can be used to target a therapeutic agent to a disease site characterized by an overexpression of an albumin-binding protein.

The invention provides for the use of a group, coupled to an agent, wherein the group is capable of binding an albumin-binding protein, such as SPARC, cubilin, or TGFβ, and the agent is a therapeutic, imaging, or delivery agent for diseases wherein the albumin-binding protein plays a dominant role and is overexpressed relative to normal tissues. Preferably, the albumin-binding protein is selected from SPARC, cubilin, or TGFβ. Most preferred, the albumin-binding protein is SPARC and the group which binds the albumin-binding protein is a SPARC recognition group. Suitable SPARC recognition groups include, but are not limited to ligands, small molecules, antibodies.

The invention also provides a method for predicting or determining the response of a human or other mammalian tumor or other proliferative disease to a chemotherapeutic agent or other anticancer agent. The method comprises (a) isolating a biological sample from the human or other mammalian, (b) detecting the expression of SPARC protein in the biological sample, and (c) quantifying the amount of SPARC protein in the biological sample. Once the amount of SPARC expressed by the tumor is determined, the effectiveness of the chemotherapeutic agent can be predicted or ascertained by, for example, correlating of the expression of SPARC to the dosage of therapeutic agent administered. The invention also provides for the use of antibody raised against SPARC as a therapeutic agent, or an imaging agent for diseases where SPARC plays a dominant role and is overexpressed relative to normal tissues.

By "predicting the response of a human or other mammalian tumor or other proliferative disease to a chemotherapeutic agent" it is meant making a judgment, based on test results combined with clinical experience, regarding the likelihood of a response before administering the chemotherapeutic agent. By "determining the response of a human or other mammalian tumor to a chemotherapeutic agent" it is meant making a judgment, based on test results combined with clinical experience, regarding the likelihood of a response after administering the chemotherapeutic agent but, before the response can be determined clinically or by conventional laboratory or imagining studies known to those of ordinary skill in the medical arts.

As used herein, "the response of a human or other mammalian tumor to a chemotherapeutic agent" refers the degree or amount that the patient improves clinically or that the tumor decreases in size or aggressiveness because of a chemotherapeutic agent. The patient can be said to improve clinically based on objective criteria, such as, e.g., performance status, physical examination, imaging studies or laboratory test results. The patient also can be said to improve clinically based subjective criteria reported by the patient, such as, e.g., pain, distress, fatigue or mental outlook. Decreases in size tumor size can be based on the primary tumor or overall tumor burden measured by any suitable method known in the art, e.g., physical examination, imaging study or laboratory value. By "decrease in tumor size" it is meant a change of at least about 10%. Further, it is desirable that a change of at least about 20% be present, preferably a change of at least about 25%, more preferably a change of at least about 33%, more preferably a change of at least about 50%, more preferably a change of at least about 90%, more preferably a change of at least about 95%, and most preferably a change of at least about 99%. By decrease in the "tumor aggressiveness" it is meant, e.g., a reduction the histologic grade, % viable cells in the tumor, % proliferating cells in the tumor, the tumor's invasiveness, the tumor's ability to metastasize or other metric of tumor aggressiveness know in the art. By "decrease in the tumor's aggressiveness" it is meant a change of at least about 10% in a measurable parameter related to tumor aggressiveness which is commonly used by those of ordinary skill in the medical arts. Further, it is desirable that a change of at least about 20% be present, preferably a change of at least about 25%, more preferably a change of at least about 33%, more preferably a change of at least about 50%, more preferably a change of at least about 90%, more preferably a change of at least about 95%, and most preferably a change of at least about 99% in a measurable parameter related to tumor aggressiveness which is commonly used by those of ordinary skill in the medical arts.

As used herein, the terms "resistant" or "resistance to a chemotherapeutic or other anticancer agent" refers to an acquired or natural resistance of a cancer sample or a mammal to a therapy, i.e., being nonresponsive to or having reduced or limited response to the therapeutic treatment, e.g., having a reduced response to a therapeutic treatment by 25% or more. Further, resistance can also be indicated by a reduced response of, for example, 30%, 40%, 50%, 60%, 70%, 80%, or more, to 2-fold, 3-fold, 4-fold, 5-fold, 10-fold, 15-fold, 20-fold or more. The reduction in response is measured by comparing with the same cancer sample or mammal before the resistance is acquired, or by comparing with a different cancer sample or a mammal who is known to have no resistance to the therapeutic treatment. As used herein, the terms "sensitive" or "sensitive to a chemotherapeutic or other anticancer agent" refers to the absence of resistance.

In addition, the invention provides for a method of treating a tumor or other proliferative disease in a mammal with a chemotherapeutic agent or other anticancer agent comprising: (a) isolating a biological sample from the mammal, (b) detecting the expression of SPARC protein or RNA in the biological sample, (c) quantifying the amount of SPARC protein or RNA in the biological sample, (d) determining if the SPARC protein or RNA is present at a level indicating the use of the chemotherapeutic agent or other anticancer agent, and (e), if, based on the SPARC protein or RNA level, it is indicated, administering a therapeutically effective amount of the chemotherapeutic agent or other anticancer agent.

The terms "treating," "treatment," "therapy," and "therapeutic treatment" as used herein refer to curative therapy, prophylactic therapy, or preventative therapy. An example of "preventative therapy" is the prevention or lessening the chance of a targeted disease (e.g., cancer or other proliferative disease) or related condition thereto. Those in need of treatment include those already with the disease or condition as well as those prone to have the disease or condition to be prevented. The terms "treating," "treatment," "therapy," and "therapeutic treatment" as used herein also describe the management and care of a mammal for the purpose of combating a disease, or related condition, and includes the administration of a composition to alleviate the symptoms, side effects, or other complications of the disease, condition. Therapeutic treatment for cancer includes, but is not limited to, surgery, chemotherapy, radiation therapy, gene therapy, and immunotherapy.

By "determining if the SPARC protein or RNA is present at a level indicating the use of the chemotherapeutic agent" it is meant that the quantified level of SPARC protein or RNA is present in the specimen from the mammal with a tumor is high enough, based on a comparison historical correlation data of SPARC level and treatment response, to indicate that the tumor can be reasonably expected to respond to the chemotherapeutic agent. By "indicating" or "indicated" it meant that, in view of the SPARC level and based on reasonable medical judgment, the chemotherapeutic agent should be used. For example, without limitation, a biopsy of a tumor can be prepared for immunohistology with anti-SPARC antibodies by preparing a thin section of the biopsy on a microscope slide. Then, the biopsy slide is stained using an anti-SPARC immunohistological protocol (see, e.g., Sweetwyne et al., J. Histochem. Cytochem. 52(6):723-33 (2004); Tai et al., J. Clin. Invest. 115(6):1492-502 (2005)) simultaneously with control slides containing sections of biopsies with known SPARC levels from other tumors sensitive to and resistant to the chemotherapeutic agent considered for use. It is a common practice in the art to grade the intensity of immunohistological staining using light microscopy. The ordinarily skilled artisan (e.g., a pathologist) can, based on comparison with the staining of the control slides, assign a staining grade (e.g., 0, 1+, 2+, 3+, 4+) to the tumor biopsy. Treatment with the chemotherapeutic agent can be "indicated" if the staining of the tumor biopsy is graded at, e.g., 3+ or 4+. Such comparisons and assignments of staining grades are well within the skill of the ordinarily skilled medical artisan (e.g., physician, pathologist, oncologist, veterinarian) treating mammals with tumors.

By "therapeutically effective amount" it is meant an amount that relieves (to some extent, as judged by a skilled medical practitioner) one or more symptoms of the disease or condition in a mammal. Additionally, by "therapeutically effective amount" is meant an amount that returns to normal, either partially or completely, physiological or biochemical parameters associated with or causative of a disease or condition. A clinician skilled in the art can determine the therapeutically effective amount of a composition in order to treat or prevent a particular disease condition, or disorder when it is administered, such as intravenously, subcutaneously, intraperitoneally, orally, or through inhalation. The precise amount of the composition required to be therapeutically effective will depend upon numerous factors, e.g., such as the specific activity of the active agent, the delivery device employed, physical characteristics of the agent, purpose for the administration, in addition to many patient specific considerations. The determination of amount of a composition that must be administered to be therapeutically effective is routine in the art and within the skill of an ordinarily skilled clinician.

The methods practiced in accordance with the invention call for a biological sample which can be isolated from the tumor or tissues involved with a proliferative disease by any suitable procedure including, without limitation, resection, biopsy, aspiration, venupuncture or combinations thereof. Alternatively, the methods practiced in accordance with the invention call for a biological sample which can be from a bodily fluid, such as, e.g., cerebrospinal fluid, blood, plasma, serum, and urine. In addition, control or reference biological samples including tumor and bodily fluid materials can be obtained from normal tissues of the same mammal, other individuals free of tumor or proliferative disease or from other tumors with known SPARC levels and known to be sensitive to or resistant to a given chemotherapeutic agent. Additionally, the methods of the invention can be practiced wherein the mammal suffering from the tumor or proliferative disease is a human.

Further, the invention provides for a kit for predicting the response of a mammalian tumor or other proliferative disease to a chemotherapeutic agent or other anticancer agent, comprising a means for the isolation of protein from the tumor, a SPARC protein detection and quantification means, control proteins, and rules for predicting the response of the tumor. The invention also provides for a kit for predicting the response of a mammalian tumor or other proliferative disease to a chemotherapeutic agent or other anticancer agent, comprising a means for the isolation of RNA from the tumor, a SPARC RNA detection and quantification means, control RNAs, and rules for predicting the response of the tumor based on the level of SPARC RNA in tumor. For example, the SPARC protein or RNA in a tumor biopsy can be "isolated" by placing a thin section of the tumor biopsy on a microscope slide. Any SPARC protein or RNA present can then be detected and quantified by immunohistological staining with an anti-SPARC antibody (see, e.g., Sweetwyne et al., J. Histochem. Cytochem. 52(6):723-33 (2004); Tai et al., J. Clin. Invest. 115(6):1492-502 (2005)) or in situ hybridization using a nucleic acid probe complementary to SPARC RNA (see, e.g., Thomas et al., Clin. Can. Res. 6:1140-49 (2000)). At the same time positive and negative control slides would be stained for SPARC protein or RNA. The ordinarily skilled artisan can readily use light microscopy to grade the staining intensity of the SPARC in the tumor biopsy (e.g., 0, 1+, 2+, 3+, 4+). The inventive kit also comprises rules for predicting the response of the tumor based on the level of SPARC protein or RNA in tumor, such as, e.g., "treatment with the chemotherapeutic agent is indicated if the staining of the tumor biopsy is graded at, e.g., 3+ or 4+" or "tumors with 3+ or 4+ staining have a high response rate." The specific rules relating to a particular embodiment of the inventive kits can readily be generated by performing retrospective or prospective correlation studies which are routine in the art and which would not require undue experimentation.

The human SPARC gene encodes a 303 amino acid SPARC protein, while mature SPARC is a 285 amino acid glycoprotein. After cleavage of the signal sequence a 32-kD secreted form is produced which migrates at 43 kD on SDS-PAGE because of glycosylation. The amino acid sequence of the complete SPARC protein is disclosed in SEQ ID NO: 1 (FIG. 1) and the nucleic acid sequence of an RNA encoding such a SPARC protein is disclosed in SEQ ID NO: 2 (presented as a cDNA sequence, i.e., with the RNA uridines ("U") as thymines ("T")) (FIG. 2).

As used herein the terms "polypeptide" and "protein" are used interchangeably. The invention provides for the detection and quantification of a SPARC polypeptide or protein such as, e.g., a polypeptide or protein comprising an amino acid sequence of SEQ ID NO: 1. The invention also provides for the detection of SPARC polypeptide, wherein the polypeptide comprises an amino acid sequence of at least about 10 sequential amino acids from the sequence of SEQ ID NO: 1, preferably at least about 15 sequential amino acids from the sequence of SEQ ID NO: 1, more preferably at least about 20 sequential amino acids from the sequence of SEQ ID NO: 1, and most preferably at least about 100 sequential amino acids from the sequence of SEQ ID NO: 1. Further, the invention provides for the detection of a SPARC polypeptide comprising a polypeptide wherein the sequence is at least about 80% homologous to the corresponding sequence of SEQ ID NO: 1, preferably at least about 90% homologous to the corresponding sequence of SEQ ID NO: 1, even more preferably at least about 95% homologous to the corresponding sequence of SEQ ID NO: 1, and even more preferably at least about 99% homologous to the corresponding sequence of SEQ ID NO: 1. By "corresponding sequence of SEQ ID NO: 1" it is meant, the sequence which aligns with the sequence of SEQ ID NO: 1 wherein the region of alignment is at least about 10 amino acids long, preferably is at least about 15 amino acids long, more preferably is at least about 20 amino acids long, more preferably is at least about 30 amino acids long, more preferably is at least about 40 amino acids long, more preferably is at least about 50 amino acids long, and even more preferably is at least about 100 amino acids long. Various methods of sequence alignment are known in the biotechnology arts (see, e.g., Rosenberg, BMC Bioinformatics 6:278 (2005); Altschul et al., FEBS J. 272(20): 5101-5109 (2005)).

The invention provides for the detection and quantification of a SPARC RNA such, e.g., an RNA comprising the nucleic acid sequence of SEQ ID NO: 2. The invention also provides for the detection of SPARC RNA, wherein the RNA comprises the nucleic sequence of at least about 15 sequential nucleotides from the sequence of SEQ ID NO: 2, preferably at least about 20 sequential nucleotides from the sequence of SEQ ID NO: 2, and more preferably at least about 30 sequential nucleotides from the sequence of SEQ ID NO: 2. Further, the invention provides for the detection of a SPARC RNA comprising a nucleic acid wherein the sequence is at least about 80% homologous to the corresponding sequence of SEQ ID NO: 2, preferably at least about 90% homologous to the corresponding sequence of SEQ ID NO: 2, even more preferably at least about 95% homologous to the corresponding sequence of SEQ ID NO: 2, and even more preferably at least about 99% homologous to the corresponding sequence of SEQ ID NO: 2. By "corresponding sequence of SEQ ID NO: 2" it is meant, the sequence which aligns with the sequence of SEQ ID NO: 2 wherein the region of alignment is at least about 15 nucleotides long, preferably is at least about 20 nucleotides long, more preferably is at least about 30 nucleotides long, more preferably is at least about 60 nucleotides long, more preferably is at least about 120 nucleotides long, more preferably is at least about 150 nucleotides long, even more preferably is at least about 200 nucleotides long. Various methods of sequence alignment are known in the biotechnology arts (see, e.g., Rosenberg, BMC Bioinformatics 6:278 (2005); Altschul et al., FEBS J. 272(20): 5101-5109 (2005)). By SPARC RNA it is meant any SPARC RNA, including but, not limited to, a SPARC mRNA, hnRNA, primary transcript or splice variant.

By "quantification" as used herein it is meant determining the amount or concentration present. The invention provides for a method of quantifying the level of SPARC protein or RNA wherein SPARC protein or RNA is overexpressed or underexpressed in the tumor relative to normal tissues, including but, not limited to, the level found in the corresponding normal tissue of origin of the tumor. Alternatively, The invention provides for a method of quantifying the level of SPARC protein or RNA wherein SPARC protein or RNA is overexpressed or underexpressed in the tumor relative to other tumors, including but not limited to, tumors of the same tissue or histology. Further, The invention provides for a method of quantifying the level of SPARC protein or RNA wherein SPARC protein or RNA is overexpressed or underexpressed in the tumor relative to other tumors, including but, not limited to, tumors which are sensitive to or resistant to a chemotherapeutic agent or combination of chemotherapeutic agents. By overexpressed or underexpressed it is meant that the levels of SPARC protein or RNA differs between the two specimens or samples by at least about 5%. Further, it is desirable that the difference between the two specimens or samples is at least about 10%, more preferably at least about 20%, more preferably at least about 50%, more preferably at least about 100%, more preferably at least about 3 fold, more preferably at least about 5 fold, and most preferably at least about 10 fold.

The invention provides for a method of quantifying the level of SPARC protein or RNA wherein SPARC protein or RNA is overexpressed or underexpressed in the test biological fluid relative to corresponding fluid from a tumor-free patient. Alternatively, The invention provides for a method of quantifying the level of SPARC protein or RNA wherein SPARC protein or RNA is overexpressed or underexpressed in the test biological fluid relative to corresponding fluid from a another patient with a tumor, including but not limited to, tumors which are sensitive to or resistant to a chemotherapeutic agent or combination of chemotherapeutic agents. By overexpressed or underexpressed it is meant that the levels of SPARC protein or RNA differs in two specimens by at least about 5%. Further, it is desirable that a difference of at least about 10% is present, preferably at least about 20%, more preferably by at least about 50%, more preferably by at least about 100%, more preferably at least about 3 fold, more preferably at least about 5 fold, and most preferably at least about 10 fold.

The invention provides methods of predicting or determining a tumor's response to a chemotherapeutic agent or other anticancer agents, methods of treating a tumor, and kits for predicting the response of a mammalian tumor to a chemotherapeutic agent or other anticancer agent, wherein the tumor is selected from the group consisting of oral cavity tumors, pharyngeal tumors, digestive system tumors, the respiratory system tumors, bone tumors, cartilaginous tumors, bone metastases, sarcomas, skin tumors, melanoma, breast tumors, the genital system tumors, urinary tract tumors, orbital tumors, brain and central nervous system tumors, gliomas, endocrine system tumors, thyroid tumors, esophageal tumors, gastric tumors, small intestinal tumors, colonic tumors, rectal tumors, anal tumors, liver tumors, gall bladder tumors, pancreatic tumors, laryngeal tumors, tumors of the lung, bronchial tumors, non-small cell lung carcinoma, small cell lung carcinoma, uterine cervical tumors, uterine corpus tumors, ovarian tumors, vulvar tumors, vaginal tumors, prostate tumors, prostatic carcinoma, testicular tumors, tumors of the penis, urinary bladder tumors, tumors of the kidney, tumors of the renal pelvis, tumors of the ureter, head and neck tumors, parathyroid cancer, Hodgkin's disease, Non-Hodgkin's lymphoma, multiple myeloma, leukemia, acute lymphocytic leukemia, chronic lymphocytic leukemia, acute myeloid leukemia, chronic myeloid leukemia. In addition, the invention provides for method of predicting or determining a tumor's response to a chemotherapeutic agent, methods of treating a tumor, and kits for predicting the response of a mammalian tumor to a chemotherapeutic agent, wherein the tumor is a sarcoma, adenocarcinoma, squamous cell carcinoma, large cell carcinoma, small cell carcinoma, basal cell carcinoma, clear cell carcinoma, oncytoma or combinations thereof. Further, the invention provides for method of predicting or determining a tumor's response to a chemotherapeutic agent, methods of treating a tumor, and kits for predicting the response of a mammalian tumor to a chemotherapeutic agent, wherein the tumor is a benign tumor or a malignant tumor. Yet further, the invention provides for method of predicting or determining a proliferative disease's response to a chemotherapeutic agent or treating a proliferative disease, including but, not limited to, where the proliferative diseases is, e.g., benign prostatic hyperplasia, endometriosis, endometrial hyperplasia, atherosclerosis, psoriasis or a proliferative renal glomerulopathy. The invention provides for embodiments wherein the tumor or proliferative disease is in mammal including but, not limited to, where the mammal is a human.

As used herein, the term "agent" or "drug" or "therapeutic agent" refers to a chemical compound, a mixture of chemical compounds, a biological macromolecule, or an extract made from biological materials such as bacteria, plants, fungi, or animal (particularly mammalian) cells or tissues that are suspected of having therapeutic properties. The agent or drug may be purified, substantially purified or partially purified. An "agent", according to the present invention, also includes a radiation therapy agent. As used herein, the term "chemotherapuetic agent" refers to an agent with activity against cancer, neoplastic, and/or proliferative diseases.

Suitable chemotherapeutic agents or other anticancer agents for use in accordance with the invention include but, are not limited to, tyrosine kinase inhibitors (genistein), biologically active agents (TNF, of tTF), radionuclides ($^{131}$I, $^{90}$Y, $^{111}$In, $^{211}$At, $^{32}$P and other known therapeutic radionuclides), adriamycin, ansamycin antibiotics, asparaginase, bleomycin, busulphan, cisplatin, carboplatin, carmustine, capecitabine, chlorambucil, cytarabine, cyclophosphamide, camptothecin, dacarbazine, dactinomycin, daunorubicin, dexrazoxane, docetaxel, doxorubicin, etoposide, epothilones, floxuridine, fludarabine, fluorouracil, gemcitabine, hydroxyurea, idarubicin, ifosfamide, irinotecan, lomustine, mechlorethamine, mercaptopurine, meplhalan, methotrexate, rapamycin (sirolimus) and derivatives, mitomycin, mitotane, mitoxantrone, nitrosurea, paclitaxel, pamidronate, pentostatin, plicamycin, procarbazine, rituximab, streptozocin, teniposide, thioguanine, thiotepa, taxanes, vinblastine, vincristine, vinorelbine, taxol, combretastatins, discodermolides, and transplatinum. Accordingly, suitable chemotherapeutic agents for use in accordance with invention include, without limitation, antimetabolites (e.g., asparaginase), antimitotics (e.g., vinca alkaloids), DNA damaging agents (e.g., cisplatin), proapoptotics (agents which induce programmed-cell-death or apoptosis) (e.g., epipodophylotoxins), differentiation inducing agents (e.g., retinoids), antibiotics (e.g., bleomycin), and hormones (e.g., tamoxifen, diethylstibestrol). Further, suitable chemotherapeutic agents for use in accordance with the invention include antiangiogenesis agents (angiogenesis inhibitors) such as, e.g., INF-alpha, fumagillin, angiostatin, endostatin, thalidomide, and the like. "Other anticancer agents" also include, without limitation, biologically active polypeptides, antibodies, lectins, and toxins. Suitable antibodies for use in accordance with the invention include, without limitation, conjugated (coupled) or unconjugated (uncoupled) antibodies, monoclonal or polyclonal antibodies, humanized or unhumanized antibodies, as well as Fab', Fab, or Fab2 fragments, single chain antibodies and the like.

Preferred chemotherapeutic agents include docetaxel, paclitaxel, and combinations thereof. "Combinations thereof" refers to both the administration of dosage forms including more than one drug, for example, docetaxel and paclitaxel, as well as the sequential but, temporally distinct, administration of docetaxel and paclitaxel (e.g., the use of docetaxel in one cycle and paclitaxel in the next). Particularly preferred chemotherapeutic agents comprise particles of protein-bound drug, including but not limited to, wherein the protein making up the protein-bound drug particles comprises albumin including wherein more than 50% of the chemotherapeutic agent is in nanoparticle form. Most preferably the chemotherapeutic agent comprises particles of albumin-bound paclitaxel, such as, e.g., Abraxane®. Such albumin-bound paclitaxel formulations can be used in accordance with the invention where the paclitaxel dose administered is from about 30 mg/m$^2$ to about 1000 mg/m$^2$ with a dosing cycle of about 3 weeks (i.e., administration of the paclitaxel dose once every about three weeks). Further, it is desirable that the paclitaxel dose administered is from about 50 mg/m$^2$ to about 800 mg/m$^2$, preferably from about 80 mg/m$^2$ to about 700 mg/m$^2$, and most preferably from about 250 mg/m$^2$ to about 300 mg/m$^2$ with a dosing cycle of about 3 weeks.

Any suitable biological sample can be isolated from the mammal in the context of the inventive method and used for polypeptide and/or RNA detection and quantification. Preferably, the biological sample is isolated from the tumor, such as by a tumor biopsy. The biological sample is isolated from the mammal using methods known in the art. Alternatively, the biological sample can be isolated from a bodily fluid of the mammal, including, for example, cerebrospinal fluid, blood, plasma, serum, or urine. In particular, many protein purification techniques are known in the art (see, e.g., Harlow & Lane, Antibodies, A Laboratory Manual, Cold Spring Harbor, pp. 421-696 (1988)).

Any suitable method for the detection and quantification of a SPARC protein can be used in accordance with the invention including, but not limited to, the use of anti-SPARC antibodies (e.g., Western blot, ELISA) (see, e.g., Sweetwyne et al., J. Histochem. Cytochem. 52(6):723-33 (2004); Tai et al., J. Clin. Invest. 115(6):1492-502 (2005)), the use of SPARC-specific binding proteins (e.g., radiolabel SPARC ligands, ELISA-like assays), two-dimensional electrophoresis, mass spectroscopy or combinations thereof (see, e.g., Nedelkov D et al., Proc. Natl. Acad. Sci. U.S.A. 102(31): 10852-7 (2005); Chen et al., Proc. Natl. Acad. Sci. U.S.A. 101(49):17039-44 (2004)). Further, immunohistochemistry can be used for the isolation, detection and quantification of SPARC protein in a sample (see, e.g., Sweetwyne et al., J. Histochem. Cytochem. 52(6):723-33 (2004); Tai et al., J. Clin. Invest. 115(6):1492-502 (2005)).

The invention provides for a method wherein the SPARC RNA is detected and quantified. Numerous methods are known in the art to isolate RNA, such as the ones described by Chomczynski (U.S. Pat. No. 5,945,515) or by DiMartino et al. (Leukemia 20(3):426-32 (2006)). Alternatively, RNA can be isolated in a form suitable for detection and quantification in accordance with the invention by the preparation of a microscope slide containing a tissue section (see, e.g., Thomas et al., Clin. Can. Res. 6:1140-49 (2000)). SPARC RNA can be detected and quantified by any suitable method known in the art including but, not limited to, in situ hybridization (see, e.g., Thomas et al., Clin. Can. Res. 6:1140-49 (2000)), Northern blot (see e.g., Wrana et al., Eur. J. Biochem. 197: 519-28 (1991)), real-time RT-PCR (see, e.g., DiMartino et al., Leukemia 20(3):426-32 (2006)), Real-time nucleic acid sequence-based amplification (see, e.g., Landry et al., J. Clin. Microbiol. 43(7):3136-9 (2005)), microarray analysis (see, e.g., Tai et al., J. Clin. Invest. 115(6):1492-502 (2005); DiMartino et al., Leukemia 20(3):426-32 (2006)) and combinations thereof.

The invention also provides a method for predicting or determining the response of a human or other mammalian tumor or other proliferative disease to a chemotherapeutic agent or other anticancer agents wherein the response of a mammalian tumor to a chemotherapeutic agent is positively or negatively correlated with SPARC levels. By "correlated with SPARC levels" it is meant, e.g., that a mutual or reciprocal relation between the tumor's response to a given chemotherapeutic agent and the level of SPARC protein or RNA detected. That is, the quality, degree, magnitude, or level of the tumor response varies with the level of the level of SPARC protein or RNA detected. A "positive correlation" is present when the quality, degree, magnitude, or level of the tumor response increases as the level of SPARC protein or RNA detected increases. A "negative correlation" is present when the quality, degree, magnitude, or level of the tumor response decreases as the level of SPARC protein or RNA detected increases. The relation between the level the tumor response and the level of SPARC protein or RNA detected can take on the form of or approximate a step-function, linear-function or logarithmic function.

In addition, the invention also provides a method for predicting or determining the response of a human or other mammalian tumor or other proliferative disease to a chemotherapeutic agent or other anticancer agents by comparing the level of SPARC protein or RNA detected to that detected in a known reference sample. Such a reference sample can be from, for example, a normal tissue or bodily fluid. Alternatively, the reference sample can be a tumor with a known SPARC level, response, sensitivity or resistance to a given chemotherapeutic agent or other anticancer agents or combinations thereof.

Further, the predicted response can be characterized as effective or as not effective such that a given chemotherapeutic agent would be used or an alternative chemotherapeutic agent would be used. As such, the predicted response can be characterized as a ratio of the response resulting from the use of one chemotherapeutic agent versus the use of another chemotherapeutic agent, e.g., the ratio of the response produced by Abraxane® to that produced by Taxotere®.

The invention further provides methods of predicting the response of a mammalian tumor or other proliferative disease to a chemotherapeutic agent or other anticancer agent comprising (a) isolating a biological sample from the mammal, (b) detecting the expression of SPARC protein or RNA in the biological sample, (c) quantifying the amount of SPARC protein or RNA in the biological sample, and (d) determining the Her2 status of the tumor or proliferative disease. The invention also provides methods of treating a tumor or other proliferative disease in a mammal with a chemotherapeutic agent or other anticancer agent comprising: (a) isolating a biological sample from the mammal, (b) detecting the expression of SPARC protein or RNA in the biological sample, (c) quantifying the amount of SPARC protein or RNA in the biological sample, (d) determining the Her2 status of the tumor or proliferative disease, (e) determining if, based on the SPARC protein or RNA level present and the Her2 status of the tumor or proliferative disease, whether the use of the chemotherapeutic agent or other anticancer agent is indicated, and (f), if indicated, administering a therapeutically effective amount of the chemotherapeutic agent or other anticancer agent.

By "determining the Her2 status of the tumor or proliferative disease" it is meant determining whether or not Her2 protein or RNA is expressed by the tumor or other proliferative disease by detecting the expression of Her2 protein or RNA in the tumor, tissue involved by another proliferative disease or other biological sample and quantifying the amount of Her2 protein or RNA present. Suitable methods for determining whether Her2 protein or RNA is expressed by a tumor or proliferative disease include, without limitation, immunohistochemistry, Western blot, ELISA, two-dimensional electrophoresis, mass spectroscopy, in situ hybridization, RNA amplification, Northern blot, microarray analysis or combinations thereof. Her2 status can be factored into predicting a response to chemotherapuetic or other anticancer agent or determining whether a chemotherapuetic or other anticancer agent is indicated either positively or negatively, as an additive factor or as a predominant factor. For example, without limitation, the absence of Her2 expression can indicate that there is no positive correlation between SPARC level and response, while the presence of Her2 expression can indicate that there is a positive correlation between SPARC level and response. The distinction between Her2 expression and its absence is within the skill of those of ordinary skill in the art and can be made based on, e.g., the results of positive and negative control samples run simultaneously with the samples from the mammal with the tumor or other proliferative disease.

Accordingly, the invention provides for a kit for predicting the response of a mammalian tumor or other proliferative disease to a chemotherapeutic agent or other anticancer agents, comprising a means for the isolation of protein or RNA from the tumor, a SPARC protein or RNA detection and quantification means, control proteins or RNAs, and rules for predicting the response of the tumor. Such a kit can, for example without limitation, be used to predict the response of a breast, ovarian or head and neck carcinoma to a chemotherapeutic agent comprising nanoparticles of albumin-bound paclitaxel. Suitable means for isolating protein or RNA and a SPARC protein or RNA detection and quantification have been described herein. Suitable control proteins or RNAs should include positive controls such as, e.g., tumor material or biological fluid from a tumor bearing mammal or isolated protein or RNA from tumor material or from a biological fluid harvested from a tumor bearing mammal. Suitable control proteins or RNAs include negative controls such as, e.g., natural tissue or biological fluid from a mammal free of tumor or isolated protein or RNA from normal tissue or biological fluid harvested from a mammal free of tumor. Controls in the kit can also include materials use to establish standard curves for quantification of SPARC protein or RNA or material from sensitive and resistant tumors. The kits of the invention can also comprising a means for determining the Her2 status of the tumor.

The inventive kits would further comprise rules for predicting the response of the tumor. Such rules would base the prediction of response to a given chemotherapeutic agent on the level of SPARC protein or RNA detected as described herein in relation to the methods of predicting or determining a response to chemotherapeutic agent. For example, a particular level of SPARC protein or RNA, based on past experience, can indicate that a chemotherapeutic agent should be used. It is within the skill of the ordinarily skilled artisan to generate, without undue experimentation, adequate data (by prospective studies, retrospective studies or a combination thereof) to determine the level of SPARC protein or RNA predictive of response to a given chemotherapeutic agent.

Hereinafter, for simplicity, all proteins, including SPARC, that bind albumin are referred to as SPARC. The SPARC protein is responsible for the accumulation of albumin in certain human tumors. As albumin is the major carrier of chemotherapeutic drugs, the expression level of SPARC is indicative of the amount of chemotherapeutic drug that penetrates and is retained by the tumor. Therefore, the expression level of SPARC is predictive of the responsiveness of the tumor to chemotherapy.

Any suitable biological sample can be isolated from the mammal of interest in the context of the inventive method. Preferably, the biological sample is isolated from the tumor, such as by a tumor biopsy. Alternatively, the biological sample can be isolated from a bodily fluid of the mammal, including, for example, cerebrospinal fluid, blood, plasma, serum, or urine. Techniques and methods for the isolation of biological samples are known to those in the art.

Any suitable pharmaceutically active agent can be used in the inventive method (e.g., a chemotherapeutic agent coupled to a SPARC recognition group), so long as the transport or binding of the active agent requires albumin. Suitable active agents include, but are not limited to, tyrosine kinase inhibitors (genistein), biologically active agents (TNF or tTF), radionuclides (e.g., $^{131}$I, $^{90}$Y, $^{111}$In, $^{211}$At, $^{32}$P, and other known therapeutic radionuclides), adriamycin, ansamycin antibiotics, asparaginase, bleomycin, busulphan, cisplatin, carboplatin, carmustine, capecitabine, chlorambucil, cytarabine, cyclophosphamide, camptothecin, dacarbazine, dactinomycin, daunorubicin, dexrazoxane, docetaxel, doxorubicin, etoposide, epothilones, floxuridine, fludarabine, fluorouracil, gemcitabine, hydroxyurea, idarubicin, ifosfamide, irinotecan, lomustine, mechlorethamine, mercaptopurine, meplhalan, methotrexate, rapamycin (sirolimus) and derivatives, mitomycin, mitotane, mitoxantrone, nitrosurea, paclitaxel, pamidronate, pentostatin, plicamycin, procarbazine, rituximab, streptozocin, teniposide, thioguanine, thiotepa, taxanes, vinblastine, vincristine, vinorelbine, taxanes, combretastatins, discodermolides, transplatinum, vascular targeting agents, anti-vascular endothelial growth factor compounds ("anti-VEGFs"), anti-epidermal growth factor receptor compounds ("anti-EGFRs"), 5-fluorouracil, and derivatives thereof.

In addition, the pharmaceutically active agent can be toxins such as ricin A, radionuclides, the Fc fragment of the antibody itself, single chain antibodies, Fab fragments, diabodies, and the like. The pharmaceutically active agents selected themselves can recognize and bind to SPARC or are suitably attached to a SPARC recognition group that recognizes SPARC, including, for example, a protein or non-protein, an antibody, Fc fragment of the antibody itself, single chain antibodies, Fab fragments, diabodies, peptides, or other non-protein small molecules.

One or more doses of one or more chemotherapeutic agents can be administered according to the inventive methods. The type and number of chemotherapeutic agents used in the inventive method will depend on the standard chemotherapeutic regimen for a particular tumor type. In other words, while a particular cancer may be treated routinely with a single chemotherapeutic agent, another may be treated routinely with a combination of chemotherapeutic agents. Methods for coupling or conjugation of suitable therapeutics, chemotherapeutics, radionuclides, etc. to antibodies or fragments thereof are well described in the art.

Diseases for which the present invention is useful include abnormal conditions of proliferation, tissue remodeling, hyperplasia, exaggerated wound healing in any bodily tissue including soft tissue, connective tissue, bone, solid organs, blood vessel and the like. Examples of diseases treatable or diagnosed by invention compositions include cancer, diabetic or other retinopathy, inflammation, arthritis, restenosis in blood vessels or artificial blood vessel grafts or intravascular devices and the like.

The types of tumor to be detected, whose response to chemotherapy is to be predicted or determined, which can be treated in accordance with the invention are generally those found in humans and other mammals. The tumors can be the result of inoculation as well, such as in laboratory animals. Many types and forms of tumors are encountered in human and other animal conditions, and there is no intention to limit the application of the methods of the present to any particular tumor type or variety. Tumors, as is known, include an abnormal mass of tissue that results from uncontrolled and progressive cell division, and is also typically known as a "neoplasm." The inventive methods are useful for tumor cells and associated stromal cells, solid tumors and tumors associated with soft tissue, such as, soft tissue sarcoma, for example, in a human. The tumor or cancer can be located in the oral cavity and pharynx, the digestive system, the respiratory system, bones and joints (e.g., bony metastases), soft tissue, the skin (e.g., melanoma), breast, the genital system, the urinary system, the eye and orbit, the brain and central nervous system (e.g., glioma), or the endocrine system (e.g., thyroid) and is not necessarily limited to the primary tumor or cancer. Tissues associated with the oral cavity include, but are not limited to, the tongue and tissues of the mouth. Cancer can arise in tissues of the digestive system including, for example, the esophagus, stomach, small intestine, colon, rectum, anus, liver, gall bladder, and pancreas. Cancers of the respiratory system can affect the larynx, lung, and bronchus and include, for example, non-small cell lung carcinoma. Tumors can arise in the uterine cervix, uterine corpus, ovary vulva, vagina, prostate, testis, and penis, which make up the male and female genital systems, and the urinary bladder, kidney, renal pelvis, and ureter, which comprise the urinary system. The tumor or cancer can be located in the head and/or neck (e.g., laryngeal cancer and parathyroid cancer). The tumor or cancer also can be located in the hematopoietic system or lymphoid system, and include, for example, lymphoma (e.g., Hodgkin's disease and Non-Hodgkin's lymphoma), multiple myeloma, or leukemia (e.g., acute lymphocytic leukemia, chronic lymphocytic leukemia, acute myeloid leukemia, chronic myeloid leukemia, and the like). Preferably, the tumor is located in the bladder, liver, ovary, kidney, gut, brain, or breast.

The SPARC protein has affinity for a wide variety of ligands. Thus, the inventive method for delivering a therapeutic agent to a site of disease is predicated on the discovery that compounds or ligands, including albumin, which have affinity for SPARC can be used to deliver therapeutic drugs to the site of disease, with little or no delivery to normal tissues.

The invention also provides for a means of transporting the therapeutic composition across the endothelial barrier from the blood vessel into the tumor interstitium. The main hurdle in antibody therapy and chemotherapy is the translocation across the endothelial barrier into tumor interstitium. Albumin utilizes the albumin receptor transport mechanism to cross the endothelial barrier. This transport mechanism could be the same as those reported by the literature (gp60 and albondin) or by other undiscovered mechanisms. It has been previously reported that the therapeutic agent piggy backed onto albumin exhibited enhanced tumoral uptake (Desai, N. et al. Increased endothelial transcytosis of nanoparticle albumin-bound paclitaxel (ABI-007) by endothelial gp60 receptors: a pathway inhibited by Taxol®, $27^{th}$ Annual San Antonio Breast Cancer Symposium (SABCS) (2004), abstract #1071). Further, enhanced translocation across the endothelial barrier can be achieved using the physiological albumin transport mechanism (Schnitzer, J. E.; Oh, P. J. Biol. Chem. 269, 6072-6082 (1994).

For small molecules, modifications can be made so that the drug affinity for albumin is increased. For formulations of small molecules, a solvent which prevents the binding of the drug to albumin may be removed. Alternatively, the small molecule may be linked to albumin, antibody against albumin, fragments thereof or ligands for an albumin-receptor such as described below.

For biologic molecules such as proteins, antibodies and fragments thereof, it is possible to engineer the biologics with an albumin binding peptide such that the biologics will exhibit an affinity for albumin. The peptide can either be an albumin binding sequence, an antibody or antibody fragment against albumin, antibody or antibody fragment against albumin carriers (such as gp60/albondin/scavenger receptor/or TGF-beta receptor), or antibody to any of the proteins found in the caveolae, the transporter of albumin. The invention also contemplates an antibody or suitable fragment thereof prepared as a chimera with one valence for SPARC and another valence for an effector of transendothelial transport such as gp60/albondin/scavenger receptor/or TGF-beta receptor, or against any of the proteins found in the caveolae of the endothelial cell.

The invention also provides a method for the destruction of SPARC expression tissues such as tumor and restenotic tissues via the complement fixation and/or recruitment of cell mediated immune response by SPARC antibody. In this case, like that of Rituxan, an anti-CD20 antibody, the effector moiety is the Fc fragment which can mediate either complement activation with direct destruction of SPARC expression cells or recruitment of immune cells to the SPARC expression tissue with resulting tissue destruction via a cell mediated immune response.

The invention also provides a method for inhibition of SPARC activity using a neutralizing antibody against SPARC. The neutralizing antibody has the ability to block the interaction of SPARC with its effectors in vivo. For example, the neutralizing antibody may block interaction of SPARC with a cell surface component or the binding of SPARC to its natural ligands such as albumin, growth factors, and $Ca^{2+}$.

The invention also provides a method for determining the response of a human or other mammalian tumor to anti-SPARC therapy. The method comprises (a) isolating a biological sample from the human, (b) detecting the expression of SPARC protein in the biological sample, and (c) quantifying the amount of SPARC protein in the biological sample. As anti-SPARC therapy relies on the binding of SPARC antibody to SPARC in disease tissue, the presence of SPARC in disease tissue is necessary for activity.

The invention further provides a method of using one or more diagnostic agents conjugated to the SPARC recognition groups, such as the antibodies or fragments thereof, as described above. The diagnostic agents include radioisotopes or radionuclides, MRI contrast agents, X-ray contrast agents, ultrasound contrast agents and PET contrast agents. Methods utilized for conjugation are known in the art.

The expression of SPARC protein in a sample can be detected and quantified by any suitable method known in the art. Suitable methods of protein detection and quantification include Western blot, enzyme-linked immunosorbent assay (ELISA), silver staining, the BCA assay (Smith et al., *Anal. Biochem.*, 150, 76-85 (1985)), the Lowry protein assay (described in, e.g., Lowry et al., *J. Biol. Chem.*, 193, 265-275 (1951)), which is a colorimetric assay based on protein-copper complexes, and the Bradford protein assay (described in, e.g., Bradford et al., *Anal. Biochem.*, 72, 248 (1976)), which depends upon the change in absorbance in Coomassie Blue G-250 upon protein binding. Tumor biopsy can be analyzed by any of the preceeding methods or it can be analyzed by immunohistochemistry using anti-SPARC antibody (either monoclonal or polyclonal) in conjunction with appropriate visualization system (i.e., HRP substrate and HRP-conjugated secondary antibody).

Any suitable antibodies against SPARC can be used in the inventive method, so long as the antibody exhibits specific binding to SPARC. The antibody can either be monoclonal or polyclonal; and can be produced either through immunization of an animal or produced through recombinant DNA technology such as phage display and in vitro mutagenesis or synthesis of the variable regions of the antibody heavy and light chain genes. Polyclonal antibodies include, but are not limited to human antibodies and humanized antibodies derived from animals such as avian (e.g., chicken), rodent (e.g., rat, mouse, hamster, guinea pig), cow, goat, sheep, rabbit and the like. Monoclonal antibodies include antibodies derived from a single clone of antibody producing cells including, but not limited to, human cells, and antibodies derived from the cells of other animal types, for example, chicken, rabbit, rat, mouse, hamster, guinea pig, cow, goat, sheep, and the like. Synthetic antibodies include antibodies produced using recombinant DNA technology via genetic engineering of the variable regions of the heavy and light chain genes. Synthetic antibodies also include chemically synthesized antibody fragments with SPARC binding activity or antibodies derived from phage display or similar technology.

For human use, in order to avoid immunogenicity and immune response, it is preferable to use humanized anti-SPARC antibody or suitable fragments such as Fab', Fab, or Fab2. Humanized antibody or fragments thereof maybe produced, for example, using one of the following established methods: 1) humanized antibody may be constructed using human IgG backbone replacing the variable CDR region with that of antibody against SPARC, where the heavy and light chain are independently expressed under separate promoters or coexpressed under one promoter with IRES sequence; 2) humanized monoclonal antibody may be raised against SPARC using a mouse engineered to have a human immune system; 3) humanized antibody against SPARC may be raised using phagemid (M13, lambda coliphage, or any phage system capable of surface presentation). To construct the full length antibody, the variable region may be transferred onto the CDR of both Heavy chain and Light chain. The coexpression of the Heavy chain and Light Chain in mammalian cells such as CHO, 293, or human myeloid cells results in full length antibody. Similarly, Fab', Fab, or Fab2 fragments and single chain antibodies can be prepared using well established methods.

Antibody against SPARC is also not limited to whole antibody or fragment of the antibody retaining the binding site for SPARC (e.g., Fab and Fab2). The antibody is also not limited to any one class of antibody, e.g., IgM, IgA, IgG, IgE, IgD, and IgY. The antibody is also not limited to divalent antibody, monovalent, or chimera with one valence for SPARC and another for an effector such tTF or ricin A. The humanized antibody is not limited to IgG. The same technologies can be used to generate all other classes of antibodies such as IgE, IgA, IgD, IgM, each having different antibody-dependent cellular cytotoxicity (ADCC) and complement dependent cytotoxicity (CDC) activities appropriate to particular disease target. Functional fragments of the antibody can be generated by limited proteolysis. These fragments can be monovalent such as Fab' or divalent, such as Fab2. Fragments can also be synthesized as single chain scfv or diabodies in *E. coli*.

The invention further provides a composition comprising a pharmaceutically active agent directly able to exert its pharmacological effect or a pharmaceutically active agent coupled to a compound capable of binding SPARC, or other or other albumin binding moiety, and a pharmaceutically acceptable carrier. The delivery agent, which may be a pharmaceutical composition, comprise the pharmaceutically active agent coupled to a SPARC recognition group is administered to a mammal, such as a human, in an amount such that a therapeutically effective amount of the pharmaceutically active agent is delivered to the mammal.

The invention also provides a method for delivering a chemotherapeutic agent to a tumor in a mammal. The method comprises administering to a human or other mammal a therapeutically effective amount of a pharmaceutical composition, wherein the pharmaceutical composition comprises the chemotherapeutic agent coupled to a compound or ligand capable of binding a SPARC protein and a pharmaceutically acceptable carrier. Descriptions of the chemotherapeutic agent, tumor, mammal, and components thereof, set forth herein in connection with other embodiments of the invention also are applicable to those same aspects of the aforesaid method of delivering a chemotherapeutic agent to a tumor.

Preferably, the pharmaceutical composition does not comprise more than 50% of the therapeutic agent in nanoparticle form. More preferably, the pharmaceutical composition does not comprise more than 10% of the therapeutic agent in nanoparticle form. Even more preferably, the pharmaceutical composition does not comprise more than 5%, or more than 4% or more than 3% of the therapeutic agent in nanoparticle form. In a more preferred embodiment, the pharmaceutical composition does not comprise more than 2% or, more than 1% of the therapeutic agent in nanoparticle form. Most preferably, the pharmaceutical composition does not comprise any of the therapeutic agent in nanoparticle form.

The invention also provides a method for delivering a chemotherapeutic agent to a tumor in a human or other mammal. The method comprises administering to a human or other mammal a therapeutically effective amount of a delivery agent, such as a pharmaceutical composition, wherein the delivery agent (e.g., pharmaceutical composition) comprises the chemotherapeutic agent coupled to the SPARC recognition group. For example, the chemotherapeutic agent can be coupled to a SPARC recognition group such as an antibody recognizing SPARC protein, or the SPARC antibody alone. Pharmaceutical compositions preferably include the chemotherapeutic agent coupled to the SPARC recognition group and a pharmaceutically acceptable carrier. Descriptions of the chemotherapeutic agent, tumor, mammal, and components thereof, set forth herein in connection with other embodiments of the invention also are applicable to those same aspects of the aforesaid method of delivering a chemotherapeutic agent to a tumor.

In other embodiments, the invention provides a method for delivering a pharmaceutically active agent by way of a SPARC recognition group to a site of disease that is characterized by overexpression of SPARC or another albumin-binding protein or marker in a human, or other animal that expresses such protein or marker. Such diseases include abnormal conditions of proliferation, tissue remodeling, hyperplasia, and exaggerated wound healing in bodily tissue (e.g., soft tissue, connective tissue, bone, solid organs, blood vessel and the like). Examples of diseases that are treatable or may be diagnosed by administering a pharmaceutical composition comprising a therapeutic agent coupled to a compound or ligand capable of binding a SPARC protein, or another albumin-binding protein, include cancer, diabetic or other retinopathy, inflammation, arthritis, restenosis in blood vessels, artificial blood vessel grafts, or intravascular devices, and the like. Descriptions of the pharmaceutically active agent, tumor, mammal, and components thereof, set forth herein in connection with other embodiments of the invention also are applicable to those same aspects of the aforesaid method of delivering a pharmaceutically active agent.

In yet other embodiments, the invention provides a method for delivering a pharmaceutically active agent (for example, SPARC antibody alone or chemotherapeutic agent conjugated to SPARC recognition group such as SPARC antibody, radiolabelled SPARC antibody and the like) to a site of disease that is characterized by overexpression of SPARC in a human, or other animal that expresses such protein or marker. Such diseases include abnormal conditions of proliferation, tissue remodeling, hyperplasia, and exaggerated wound healing in bodily tissue (e.g., soft tissue, connective tissue, bone, solid organs, blood vessel and the like). Examples of diseases that are treatable or diagnosed by administering a pharmaceutical composition comprising anti-SPARC therapy, include cancer, diabetic or other retinopathy, inflammation, arthritis, restenosis in blood vessels, artificial blood vessel grafts, or intravascular devices, and the like. Descriptions of the pharmaceutically active agent, tumor, mammal, and components thereof, set forth here in connection with other embodiments of the invention also are applicable to those same aspects of the aforesaid method of delivering a pharmaceutically active agent.

In other embodiments, the inventive method comprises administering to a mammal a therapeutically effective amount of a pharmaceutical composition comprising a chemotherapeutic agent coupled to a compound or ligand capable of binding SPARC protein. The chemotherapeutic agent can be coupled to the compound or ligand capable of binding SPARC protein using any suitable method. Preferably, the chemotherapeutic agent is chemically coupled to the compound via covalent bonds including, for example, disulfide bonds.

The invention also provides a method comprising administering to a mammal a therapeutically effective amount of a pharmaceutical composition comprising a chemotherapeutic agent or radioactive element coupled to a SPARC recognition group. The chemotherapeutic or radioactive agent can be coupled to the antibody recognizing SPARC using any suitable method. Preferably, the chemotherapeutic agent can be chemically coupled to the compound via covalent bonds including, for example, disulfide bonds.

Preferably, the compound or ligand useful in the inventive method is capable of binding the SPARC protein. In a preferred embodiment of the invention, the compound is a ligand that binds a SPARC protein. Examples of suitable ligands include calcium cation ($Ca^{2+}$), copper cation ($Cu^{2+}$), iron cation ($Fe^{2+}$), platelet derived growth factor (PDGF), vascular endothelial growth factor (VEGF), collagen (e.g., collagen I, collagen II, collagen III, collagen IV, collagen V, and collagen IX), vitronectin, thrombospondin-1, endothelial cells, platelets, albumin, and hydroxyapatitecations. In another preferred embodiment of the invention, the compound is a small molecule. The term "small molecule" refers to any molecule having a molecular weight less than about 600. Examples of suitable small molecules include a protein, a nucleic acid, a carbohydrate, a lipid, a coenzyme (e.g., a vitamin), an antigen, a hormone, and a neurotransmitter. Preferably, the small molecule is a chemical (e.g., an organic or inorganic chemical) a peptide, or peptide mimetic, a protein, or a carbohydrate. In yet another preferred embodiment of the invention, the compound is an antibody that is directed against a SPARC protein. Any suitable antibody, or fragment thereof, that binds to a SPARC protein can be used in the inventive method.

SPARC expression in tumor tissues has been demonstrated in almost all cancer types. There has been evidence that elaboration of SPARC on tumor tissues can be either derived from tumoral expression of SPARC or by stromal cells. The SPARC phenotype of the tumor can be converted from SPARC negative to SPARC positive by administration of exogenous SPARC. Accordingly, the SPARC positive tumor would then become sensitive to chemotherapeutic agents. Alternatively, SPARC could be radiolabeled or conjugated with various toxins to confer on it the ability to kill the tumor directly or indirectly.

SPARC can be synthesized and purified using known technologies. Cells expressing exogenous SPARC can be generated by placing the SPARC structural gene/cDNA under the control of strong promoter/translation start and the vector transfected into mammalian cells to drive the expression of SPARC in these cells. Alternatively, SPARC can be expressed using bacculovirus or other viruses such as adenovirus. SPARC expressed by these cells can be purified by traditional purifications methods such as ionic exchange, size exclusion, or C18 chromatography. The purified SPARC can be formulated in saline with preservatives and administered intravenously, by aerosol, by subcutaneous injection, or other methods.

The invention also provides a method for delivering a chemotherapeutic agent to a tumor in a mammal. The method comprises administering to a mammal a therapeutically effective amount of a pharmaceutical composition, wherein the pharmaceutical composition comprises the chemotherapeutic agent coupled to a SPARC protein capable of binding albumin and a pharmaceutically acceptable carrier. Descriptions of the chemotherapeutic agent, tumor, mammal, and components thereof, set forth herein in connection with other embodiments of the invention also are applicable to those same aspects of the aforesaid method of delivering a chemotherapeutic agent to a tumor.

For use in vivo, the chemotherapeutic agent coupled to a compound or ligand capable of binding the SPARC protein desirably is formulated into a pharmaceutical composition comprising a physiologically acceptable carrier. Any suitable physiologically acceptable carrier can be used within the context of the invention, and such carriers are well known in the art.

For use in vivo, the anti-SPARC therapy agent desirably is formulated into a pharmaceutical composition comprising a physiologically acceptable carrier. Any suitable physiologically acceptable carrier can be used within the context of the invention, and such carriers are well known in the art.

The carrier typically will be liquid, but also can be solid, or a combination of liquid and solid components. The carrier desirably is a physiologically acceptable (e.g., a pharmaceutically or pharmacologically acceptable) carrier (e.g., excipient or diluent). Physiologically acceptable carriers are well known and are readily available. The choice of carrier will be determined, at least in part, by the location of the target tissue and/or cells, and the particular method used to administer the composition.

Typically, such compositions can be prepared as injectables, either as liquid solutions or suspensions; solid forms suitable for using to prepare solutions or suspensions upon the addition of a liquid prior to injection can also be prepared; and the preparations can also be emulsified. The pharmaceutical formulations suitable for injectable use include sterile aqueous solutions or dispersions; formulations containing known protein stabilizers and lyoprotectants, formulations including sesame oil, peanut oil or aqueous propylene glycol, and sterile powders for the extemporaneous preparation of sterile injectable solutions or dispersions. In all cases, the formulation must be sterile and must be fluid to the extent that easy syringability exists. It must be stable under the conditions of manufacture and storage and must be preserved against the contaminating action of microorganisms, such as bacteria and fungi. Solutions of the active compounds as free base or pharmacologically acceptable salts can be prepared in water suitably mixed with a surfactant, such as hydroxycellulose. Dispersions can also be prepared in glycerol, liquid polyethylene glycols, and mixtures thereof and in oils. Under ordinary conditions of storage and use, these preparations contain a preservative to prevent the growth of microorganisms.

The chemotherapeutic agent (e.g., anti-SPARC therapy) coupled to a compound or ligand which binds a SPARC protein can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such as organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

The composition can further comprise any other suitable components, especially for enhancing the stability of the composition and/or its end-use. Accordingly, there is a wide variety of suitable formulations of the composition of the invention. The following formulations and methods are merely exemplary and are in no way limiting.

Formulations suitable for administration via inhalation include aerosol formulations. The aerosol formulations can be placed into pressurized acceptable propellants, such as dichlorodifluoromethane, propane, nitrogen, and the like. They also can be formulated as non-pressurized preparations, for delivery from a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of a sterile liquid excipient, for example, water, for injections, immediately prior to use. Extemporaneous injection solutions and suspensions can be prepared from sterile powders, granules, and tablets of the kind previously described. In a preferred embodiment of the invention, the chemotherapeutic agent coupled to a compound which binds a SPARC protein (e.g., anti-SPARC therapy) is formulated for injection (e.g., parenteral administration). In this regard, the formulation desirably is suitable for intratumoral administration, but also can be formulated for intravenous injection, intraperitoneal injection, subcutaneous injection, and the like.

Formulations suitable for anal administration can be prepared as suppositories by mixing the active ingredient with a variety of bases such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

In addition, the composition can comprise additional therapeutic or biologically-active agents. For example, therapeutic factors useful in the treatment of a particular indication can be present. Factors that control inflammation, such as ibuprofen or steroids, can be part of the composition to reduce swelling and inflammation associated with in vivo administration of the pharmaceutical composition and physiological distress.

The following examples further illustrate the invention but should not be construed as in any way limiting its scope.

EXAMPLE 1

This example illustrates the co-localization of SPARC with albumin in an MX-1 tumor xenograft.

Paclitaxel albumin nanoparticles (Abraxane, ABX or ABI-007) have been shown to have an improved response rate over Taxol (TAX) in a Phase 3 metastatic breast cancer trial (33% vs. 19%, $p<0.0001$) (see, e.g., O'Shaughnessy, SABCS). Albumin-mediated transendothelial transport of paclitaxel (P) and increased intratumoral accumulation of paclitaxel for ABX versus TAX was demonstrated recently (see, e.g., Desai, SABCS 2003). Albumin binds to SPARC (see, e.g., Schnitzer, *J. Biol. Chem.*, 269, 6072-82 (1994)).

The MX-1 tumor cell line is derived from a human breast cancer. Serial cryosections of human MX-1 tumor xenograft, human primary breast tumor tissues (n=141), and normal human breast tissue (n=115) were immunostained and scored (0-4) for albumin, SPARC (using anti-SPARC antibody), and caveolin-1 staining. Cultured MX-1 cells also were immunostained for SPARC. Paclitaxel albumin nanoparticles (Abraxane, ABX or ABI-007) and Taxol (TAX) were prepared with radioactive paclitaxel (P) (20 mg/kg IV), and were used to determine the biodistribution of paclitaxel in normal tissues of athymic mice.

Albumin staining in the MX-1 tumor was focal and co-localized with SPARC (FIG. 3). Caveolin-1 staining confirmed that blood vessel density in albumin-containing areas was no different from albumin-free areas. SPARC expression by MX-1 cultured cells was confirmed by positive staining with anti-SPARC antibody. Paclitaxel accumulation in normal tissues (SPARC negative) was significantly lower for ABX as compared to TAX (p<0.004) for 7/10 tissues. 46% of the human primary breast tumors exhibited strong SPARC staining (score >2), as compared to 1% for normal tissues (p<0.0001). In a subset of 50 tumor tissues, SPARC expression did not correlate with staging, ER status, or PgR status; however, there was trend for high SPARC expression among p53-negative tumors.

The co-localization of albumin and SPARC suggests that SPARC, by its albumin binding activity, may behave as an intratumoral target for albumin binding in breast tumors. As transport of paclitaxel in ABX is dependent on albumin (see, e.g., Desai SABCS, 2003), this may explain the improved tumor accumulation of ABX as compared to TAX. ABX accumulation in normal tissues was lower than for TAX, consistent with lack of SPARC expression in normal tissues. Screening of patients for SPARC allows for the identification of patients more responsive to ABX. The presence of SPARC in these tumors allows for targeting and therapy using anti-SPARC antibody.

EXAMPLE 2

This example illustrates the expression of SPARC in MX-1 tumor cells.

MX-1 cells were cultured on a coverslip and stained with an antibody directed against human SPARC using methods known in the art. Antibody staining was observed, which demonstrates that MX-1 is expressing SPARC. These results suggest that SPARC expression detected in MX-1 tumor cells is a result of SPARC secretion by MX-1 tumor cells. Staining was more intense for MX-1 tumor cells than that of normal primary cells such as HUVEC (human umbiblical vein endothelial cells), HLMVEC (Human lung microvessel endothelial cells), and HMEC (Human mammary epithelial cells). Though the majority of the SPARC staining was internal SPARC, significant level of surface SPARC was detected as demonstrated by confocal miscroscopy and staining of unpermeabilized cells.

EXAMPLE 3

This example illustrates the overexpression of SPARC protein in human breast carcinoma cells.

SPARC expression in human breast carcinoma cells was determined using a tumor array from Cybrdi, Inc. (Gaithersburg, Md.). The results of this analysis are set forth in Table 1. Intensity of staining was scored from "Negative" to 4+, with the higher number corresponding to greater intensity of overexpression. 49% of breast carcinoma stained positive (2+ and above) for SPARC, as compared to 1% of normal tissue (p<0.0001).

| | SPARC Staining (%) | | | | | |
|---|---|---|---|---|---|---|
| | Negative | −/+ | 1+ | 2+ | 3+ | 4+ |
| Carcinoma Cells | 31 (34%) | 14 (15%) | 1 (1%) | 11 (12%) | 9 (10%) | 25 (27%) |
| Normal Cells | 93 (89%) | 7 (7%) | 4 (4%) | 1 (1%) | 0 (0%) | 0 (0%) |

EXAMPLE 4

This example illustrates endothelial receptor (gp60)-mediated caveolar transcytosis of paclitaxel albumin nanoparticles (ABI-007).

Paclitaxel (P) albumin nanoparticles (Abraxane, ABX or ABI-007) demonstrated improved response rate over Taxol in a phase III metastatic breast cancer trial (33% vs 19%, p<0.0001) (SABCS, O'Shaughnessy et al, 2003). Cremophor in Taxol (TAX) entraps P in micelles in plasma, reducing the paclitaxel available for cellular partitioning (see, e.g., Sparreboom et al., Cancer. Res., 59, 1454 (1999)). Studies in athymic mice have shown 30-40% higher intratumor paclitaxel concentrations with ABX as compared to equal doses of TAX (SABCS, Desai et al, 2003). Albumin is transported across endothelial cells (EC) by specific receptor (gp60)-mediated caveolar transport (see, e.g., John et al., Am. J. Physiol., 284, L187 (2001)). It was hypothesized that albumin-bound paclitaxel in ABX may be transported across tumor microvessel EC by gp60, and this mechanism may be particularly active for ABX as compared to TAX.

A series of experiments were performed to evaluate binding and transport of paclitaxel by human umbilical vein endothelial cells (HUVEC) and human lung microvessel endothelial cells (HLMVEC) for ABX and TAX. Fluorescent paclitaxel (FP) was used as a probe and fluorescent ABX and TAX were formulated with FP to probe the binding and transport of paclitaxel across EC monolayers grown on a transwell apparatus.

Binding of paclitaxel to cells (HUVEC) was 10× higher for ABX than TAX. The transport of paclitaxel from ABX across EC monolayers was enhanced by 2-3 fold and 2-4 fold for HUVEC and HMVEC, respectively, as compared to TAX. Transport was dependent on albumin. Transport of paclitaxel from ABX was inhibited by the presence of anti-SPARC antibody, which is known to bind gp60, the receptor required for caveolar albumin transcytosis. Known inhibitors of calveolar transcytosis, NEM and β-methyl cyclodextrin (BMC), also inhibited the transport of paclitaxel from ABX across the endothelial monolayers (FIG. 4). Inhibition of caveolar transport decreased transport of P from ABX to the level of TAX transport.

These results demonstrate that paclitaxel from ABX is actively transported across EC by gp60-mediated caveolar transcytosis, whereas P from TAX appears to be transported at a 2-4 fold lower rate primarily by a paracellular (non-caveolar) mechanism. This pathway may in part be responsible for increased intratumoral concentrations of paclitaxel seen for ABX relative to TAX. Cremophor in TAX inhibits transcytosis of paclitaxel across endothelial cells.

EXAMPLE 5

This example demonstrates correlation of SPARC overexpression with high response rates using nanoparticle albumin-bound paclitaxel (ABI-007) in squamous head and neck cancers.

In phase I and II clinical studies of patients with squamous cell carcinoma (SCC) of head and neck (H&N) and anal canal, response rates of 78% and 64% were observed, respectively, for intra-arterially delivered Nanoparticle Albumin-Bound Paclitaxel (Abraxane®, ABX or ABI-007) (see, e.g., Damascelli et al., Cancer, 92(10), 2592-2602 (2001), and Damascelli et al., AJR, 181, 253-260 (2003)). In comparing in vitro cytoxicity of ABX and Taxol (TAX), we observed that a squamous cervix (A431) line demonstrated improved $IC_{50}s$ for ABX (0.004 μg/ml) vs TAX (0.012 μg/ml). Albumin-mediated transendothelial caveolar transport of paclitaxel (P) and increased intratumoral accumulation of P for ABX vs TAX was demonstrated recently (see, e.g., Desai, SABCS 2003).

Human H&N tumor tissues (n=119) and normal human H&N tissue (n=15) were immunostained and scored (0-4) for SPARC staining using a tumor and normal tissue array. Immunostaining was performed using polyclonal rabbit anti-SPARC antibody. In a new phase I dose escalation study (ABX given IV over 30 minutes q3w), a subset of head and neck cancer patients (n=3) were analyzed for response to ABX.

SPARC was overexpressed (score >2) in 60% (72/119) of the H&N tumors versus 0% (0/15) in normal tissues (p<0.0001). In the phase I study, 2/3 H&N patients achieved partial response (PR) after 2 cycles of treatment at dose levels of 135 mg/m² (1 pt) and 225 mg/m² (1 pt). A third patient at 260 mg/m² progressed.

SPARC was found to be overexpressed in 60% of squamous H&N tumors. This may explain the high single-agent activity of ABX seen previously in squamous H&N cancers due to binding of albumin-bound paclitaxel to SPARC expressed in these tumors. 2/3 patients with squamous H&N tumors achieved PR in a new phase I study.

| SPARC Staining: | 0 | −/+ | 1 | 2 | 3 | 4 |
|---|---|---|---|---|---|---|
| H&N Tumor Array: | | | | | | |
| Carcinoma | 17 (14%) | 14 (12%) | 16 (13%) | 23 (19%) | 20 (17%) | 29 (24%) |
| Normal | 13 (87%) | 0 (0%) | 2 (13%) | 0 (0%) | 0 (0%) | 0 (0%) |

Human H&N tumor tissues (n=119) and normal human H&N tissue (n=15) were immunostained and scored (0-4) for SPARC staining using a tumor and normal tissue array. Immunostaining was performed using polyclonal rabbit anti-SPARC antibody. SPARC was overexpressed (score >2) in 60% (72/119) of the H&N tumors versus 0% (0/15) in normal tissues (p<0.0001). This may explain the high single-agent activity of ABX seen previously in squamous H&N cancers due to binding of albumin-bound paclitaxel to SPARC expressed in these tumors.

In a new phase I dose escalation study (ABX given IV over 30 minutes q3w), a subset of head and neck cancer patients (n=3) were analyzed for response to ABX. In the phase I study, 2/3 H&N patients achieved partial response (PR) after 2 cycles of treatment at dose levels of 135 mg/m² (1 pt) and 225 mg/m² (1 pt). A third patient at 260 mg/m² progressed. Tumor tissues from these patients were stained for SPARC and 1 responding patients showed strong overexpression for SPARC.

In another phase II clinical study of 54 patients with squamous cell carcinoma of head and neck treated with intra-arterial ABX, an overall response rate of 78% was noted. Cancer biopsies from 16 patients in this study receiving intra-arterial ABX were evaluated for SPARC expression and correlation with clinical response. Staining with anti-SPARC polyclonal antibody (R&D Systems, Minneapolis, Minn., USA) was scored on a 0-4 scale (032 no staining, 4=strong positive). Positive SPARC expression was identified as >2+ staining and negative SPARC expression was identified as <2+ staining. The ABX—responders exhibited higher incidence of SPARC expression (10/11, 91%) versus nonresponders (2/5, 40%) (p=0.06.) ABX—response was significantly higher for SPARC-positive patients (10/12=83%) versus SPARC-negative patients (1/4=25%) (p=0.06). In addition, the SPARC-negative patients exhibited significantly lower response rate than the overall response rate in the study (including patients treated with ABX or other chemotherapeutic agents) (1/4, 25% vs. 42/54, 78%; p<0.05)).

EXAMPLE 6

This example illustrates the internalization of labeled albumin into MIX-1 tumor cells and colocalization within the MIX-1 cell with intracellular SPARC expression.

MX-1 cells were cultured on a coverslip and permeabilized with suitable agents. Cells were exposed to fluorescent albumin and following washing were exposed to SPARC antibody. This was followed by exposure to a secondary antibodies having a different fluorescent tag than the albumin. It was surprisingly observed that the labeled albumin colocalised with the presence of SPARC within the cell indicating that albumin was rapidly internalized and targeted intracellular SPARC.

EXAMPLE 7

This example demonstrates an increase in endothelial transcytosis via gp60 (albumin receptor) of pharmaceutical compositions comprising paclitaxel and albumin as compared to Taxol.

Human lung microvessel endothelial cells (HLMVEC) were grown to confluence on a transwell. The inventive pharmaceutical composition comprising paclitaxel and albumin, or Taxol containing fluorescent paclitaxel (Flutax) at a concentration of 20 μg/mL, was added to the upper transwell chamber.

The transport of paclitaxel by transcytosis from the upper chamber to the lower chamber was monitored continuously using a fluorometer. A control containing only Flutax without albumin was also used. The control with Flutax showed no transport, validating the integrity of the confluent HLMVEC monolayer. Transport of paclitaxel from the albumin-paclitaxel composition was much faster than paclitaxel from Taxol in the presence of 5% HSA (physiological concentration). Transport rate constants ($K_t$) for the albumin-paclitaxel composition and Taxol were 1.396 $h^{-1}$ and 0.03 $h^{-1}$, respectively. The total amount of paclitaxel transported across the monolayer was three times higher for the albumin-paclitaxel composition than Taxol. Thus, the use of albumin or other suitable mimetic including antibodies or fragments against the gp60 receptor or other endothelial cell receptor can assist in the transport of a desired therapeutic agent across the endothelial barrier into the tumor interstitium.

EXAMPLE 8

This example demonstrates the specific binding of anti-SPARC antibody to SPARC.

Whole cell extract was prepared from HUVEC cells by sonication. The protein was separated on a s5-15% SDS-PAGE, transferred onto PVDF membrane and visualized with a polyclonal antibody against SPARC and a monoclonal antibody against SPARC. Both antibodies reacted to a single band at 38 kDa, the correct molecular weight for SPARC. When MX-1 was analyzed by the same method, SPARC was detected in both the clarified cell lysate or the membrane rich membrane fraction.

EXAMPLE 9

This example demonstrates the absence of SPARC expression in normal tissues.

Normal human and mouse tissue were immunostained and scored (0-4) for SPARC staining using a tumor and normal tissue array. Immunostaining was performed using polyclonal rabbit anti-SPARC antibody. SPARC was not expressed in any of the normal tissues, with the exception of the esophagus. Likewise, SPARC was not expressed in any of the normal mouse tissue, except the kidney of the female mouse. However, it is possible that this expression was due to follistatin which is homologous to SPARC.

SPARC Expression in Human Normal Tissues

| | |
|---|---|
| Stomach | 0/8 |
| Colon | 0/9 |
| Rectum | 0/15 |
| Liver | 0/14 |
| Spleen | 0/10 |
| Lung | 0/14 |
| Kidney | 1/14 |
| Brain | 1/14 |
| Testis | 0/8 |
| Prostate | 0/3 |
| Heart | 0/9 |
| Tonsil | 0/10 |
| Lymph Nodes | 0/10 |
| Appendix | 0/10 |
| Esophagus | 5/5 |
| Pancreas | 0/5 |
| Eyeball | 0/5 |
| Ovary | 0/5 |

Mouse Normal Tissues

| | |
|---|---|
| Liver | 0/19 |
| Kidney (M) | 0/8 |
| Kidney (F) | 6/8 |
| Lung | 0/16 |
| Muscle | 0/20 |
| Brain | 0/20 |
| Heart | 0/18 |
| Stomach | 0/20 |
| Spleen | 0/20 |

EXAMPLE 10

This example demonstrates the superiority of Abraxane (nanoparticle albumin-bound paclitaxel, "ABX") to Taxotere (docetaxel formulated with Tween 80 and ethanol, "TAT") and that the relative response to ABX positively correlates with SPARC expression in the Her2-positive xenografts tested.

A murine tumor xenograft model system was used to compare the efficacy of ABX versus TAT in Her2-negative xenografts of the MX-1 human breast carcinoma and LX-1 human lung carcinoma cell lines. In the MX-1 study 8 animals were used in each of three groups: TAT (once per week for three weeks, iv) at 15 mg/kg; ABX (once per week for three weeks, iv) at 15 mg/kg, and saline (once per week for three weeks, iv). Each animal's weight and tumor size obtained weekly for three weeks. In the LX-1 study 8 animals were used in each of three groups: TAT (once every four days for three cycles, iv) at 15 mg/kg; ABX (once every four days for three cycles, iv) at 50 mg/kg or 120 mg/kg, and saline (once every four days for three cycles, iv). Each animal's weight and tumor size obtained weekly for three weeks.

Xenograft tumor Her2 and SPARC status were determined by immunohistochemistry using a monoclonal anti-human Her2 antibody and a polyclonal anti-human SPARC antibody. The slides were scored using a 0-4 scale, 0 being negative and 4 being strong positive.

Figure 5A:
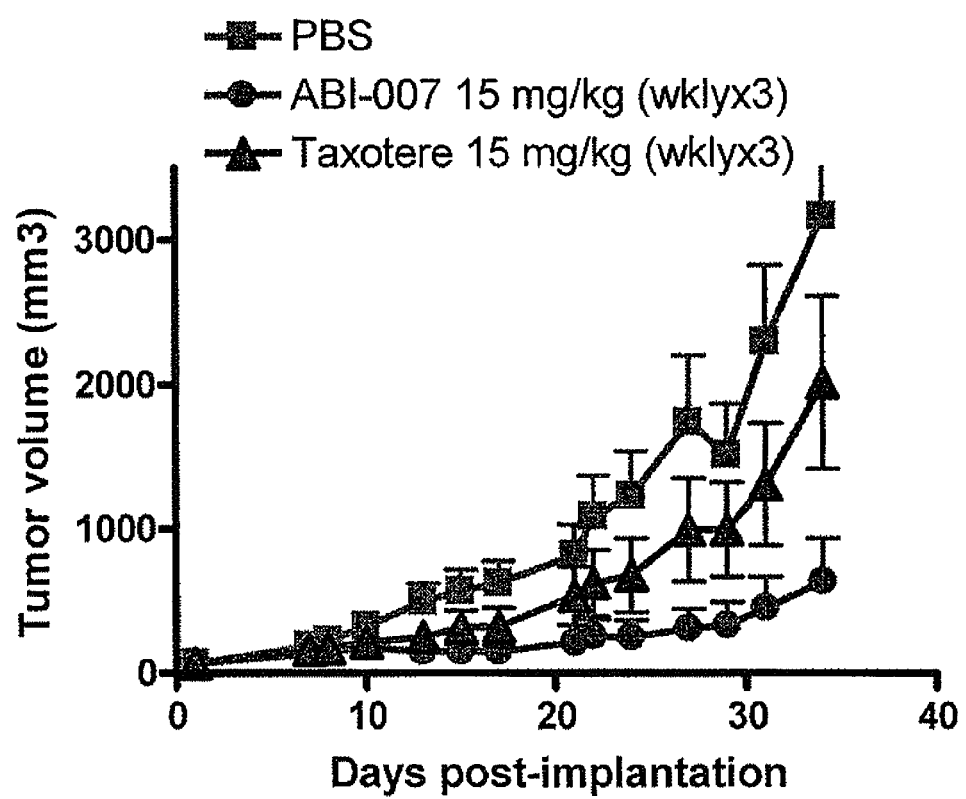
FIG. 5A-B illustrate the comparative efficacy (A, tumor volume) and toxicity (B, % weight loss) of Abraxane and Taxotere for the treatment of a MX-1 xenograft.
Figure 5B:
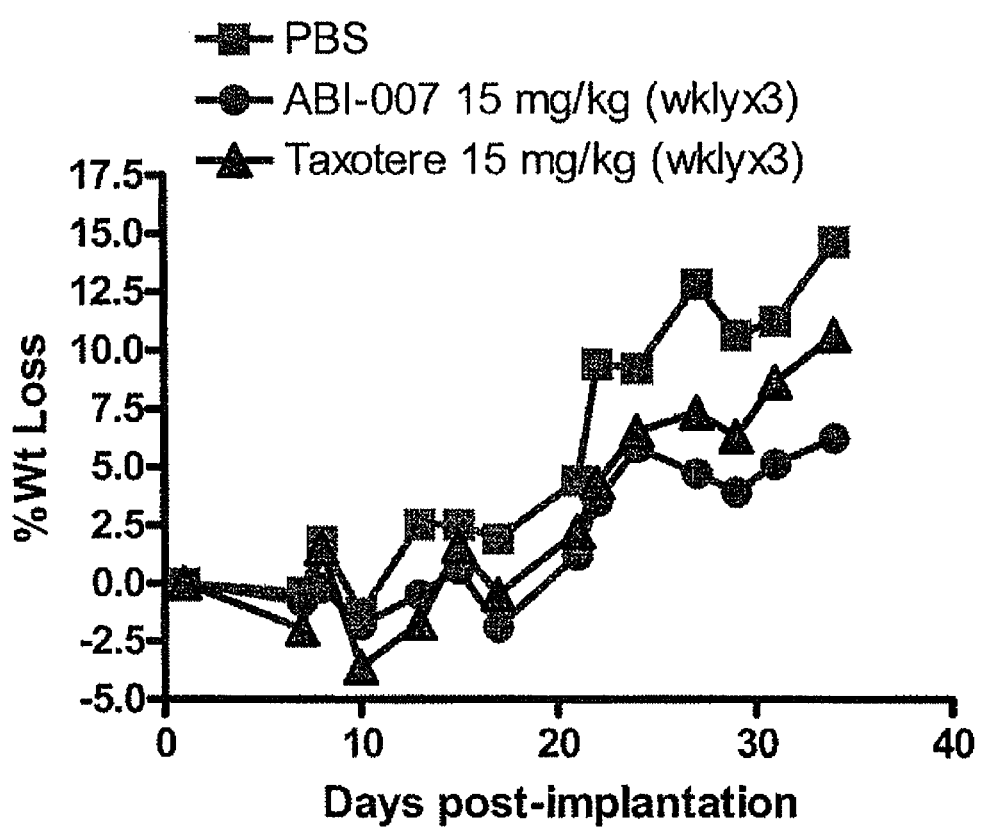
Figure 6A:
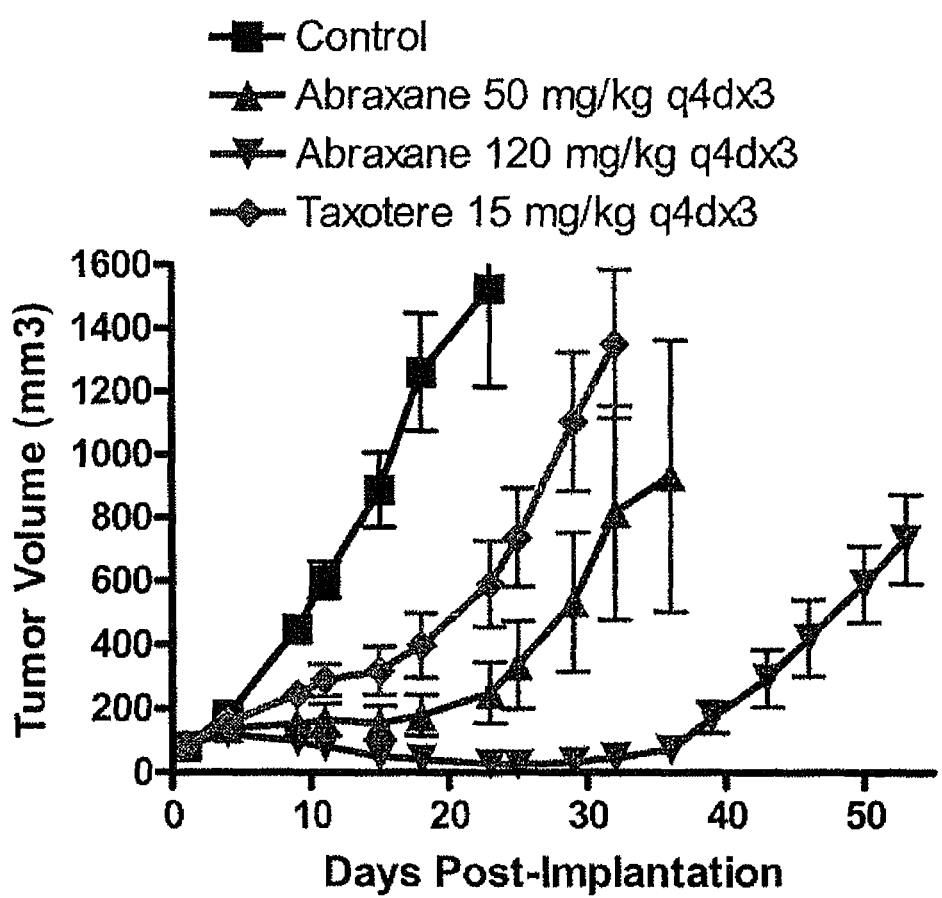
FIG. 6A-B illustrate the comparative efficacy (A, tumor volume) and toxicity (B, % weight loss) of Abraxane and Taxotere for the treatment of a LX-1 xenograft.
Figure 6B:
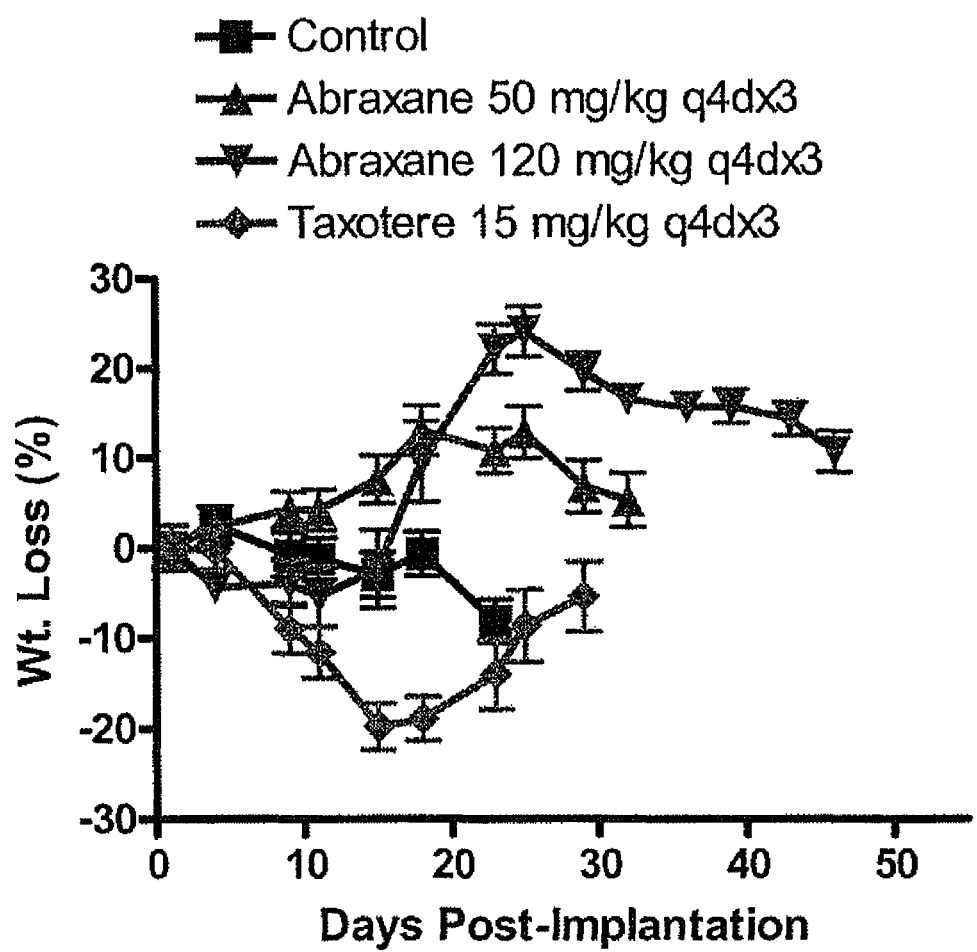

In the MX-1 study, ABX at equidose was more effective than TAT ($p<0.0001$, ANOVA statistic) (see FIG. 5A). For the LX-1 cells, ABX was more effective than TAT (15 mg/kg) at both dose levels ($p=0.0001$ for ABX 50 mg/kg and $p<0.0001$ for ABX 120 mg/kg) (see FIG. 6A). However, ABX response did not correlate with SPARC level by immunohistochemistry (see FIG. 7).

In a second study, a murine tumor xenograft model system was used to compare the Efficacy of ABX versus TAT in three Her2-positive xenografts (HT29: human colonic carcinoma cell line, PC3: human prostate carcinoma cell line, MDA-MB-231: human breast carcinoma cell line). Thirty two mice were used for each xenograft with eight animals treated with TAT (once every four days for three cycles, iv) at 15 mg/kg, eight animals treated with ABX (once every four days for three cycles, iv) at 50 mg/kg, eight animals treated with ABX (once every four days for three cycles, iv) at 120 mg/kg, and eight control animals treated with saline (once every four days for three cycles, iv). Each animal's weight and tumor size obtained for each of the three weeks.

The Her2 and SPARC status were determined by immunohistochemistry using a monoclonal anti-human Her2 antibody and a polyclonal anti-human SPARC antibody. The slides were scored using a 0-4 scale, 0 being negative and 4 being strong positive.

Figure 8A:
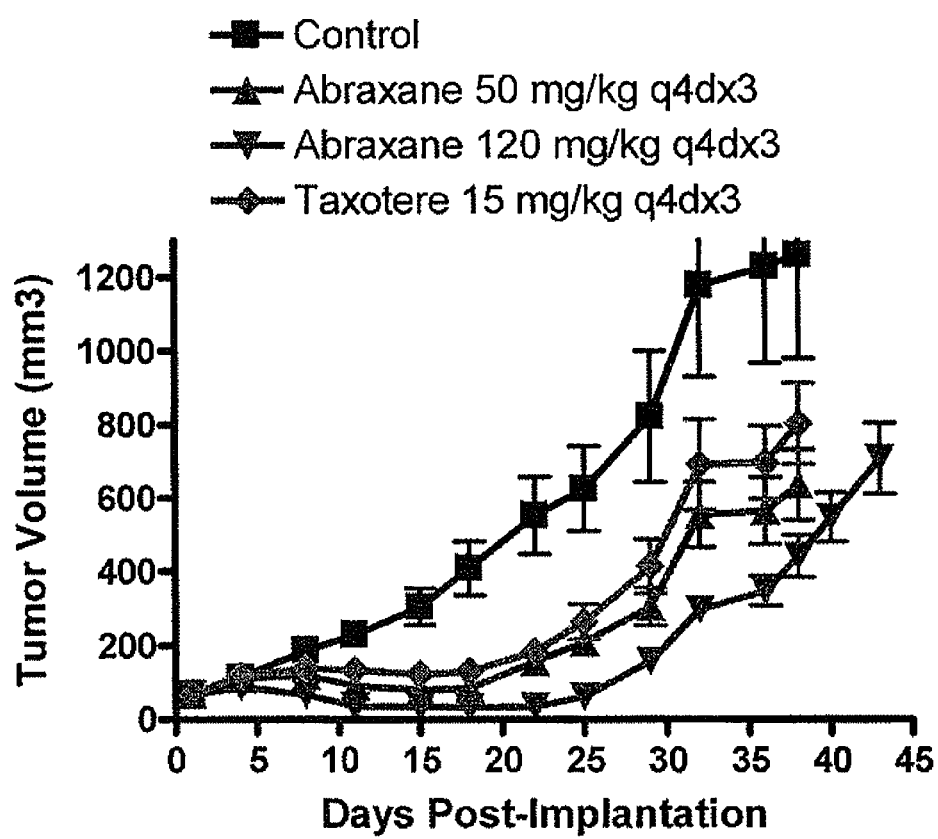
FIG. 8A-B illustrate the comparative efficacy (A, tumor volume) and toxicity (B, % weight loss) of Abraxane and Taxotere for the treatment of a HT29 xenograft.
Figure 8B:
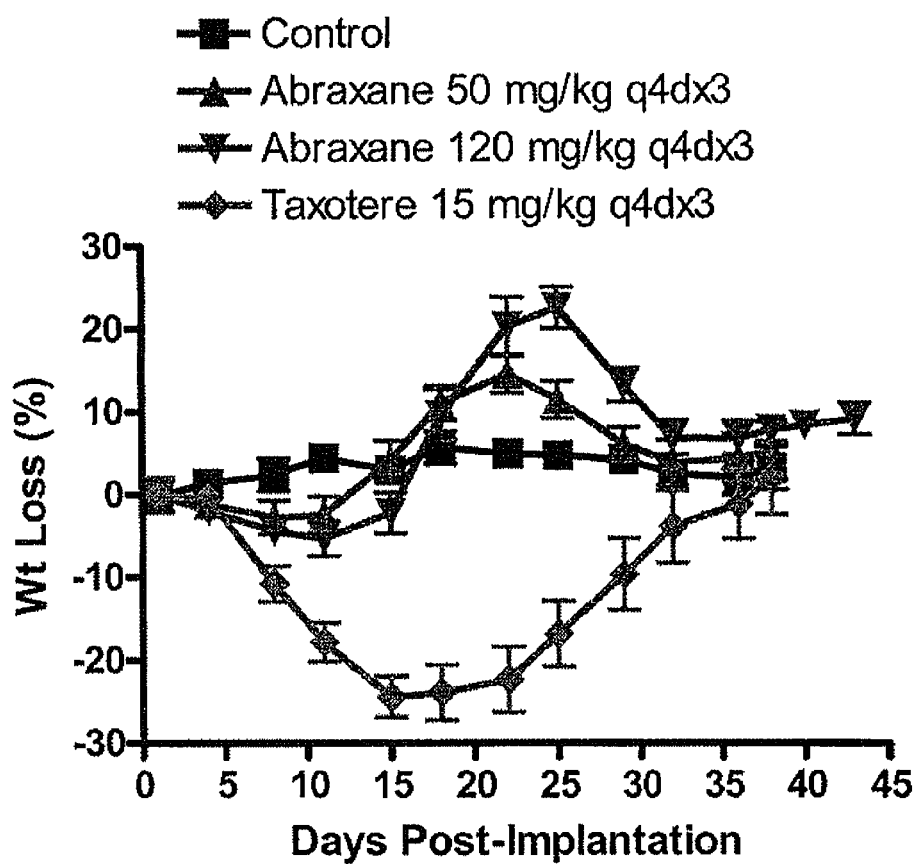
Figure 9A:
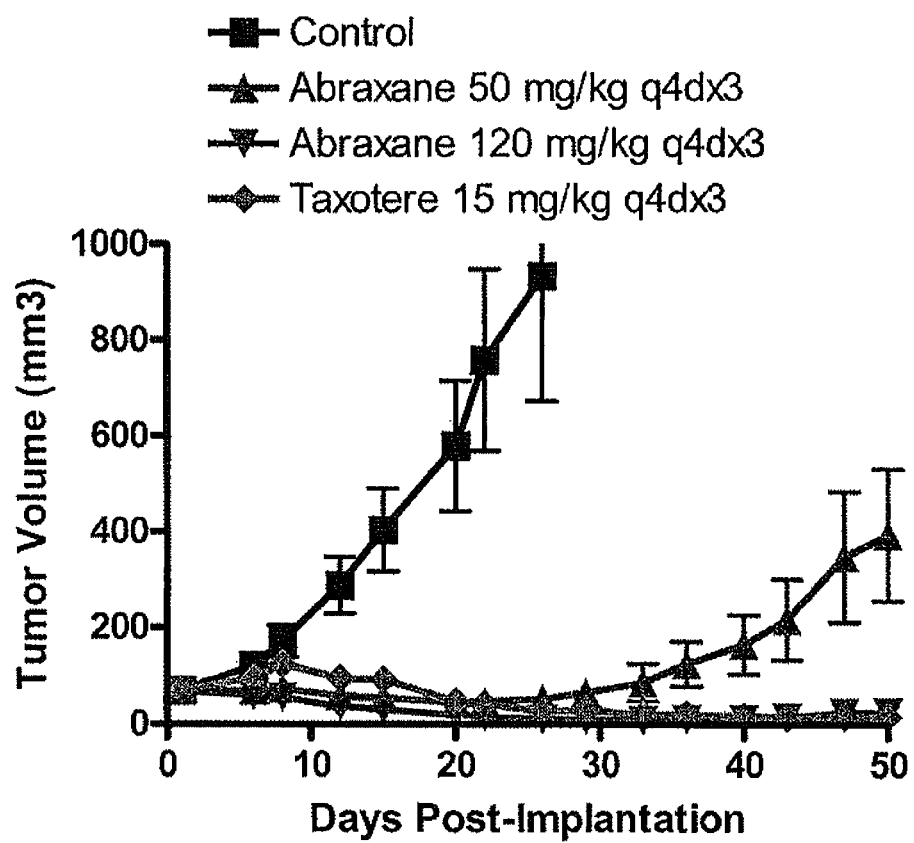
Figure 10A:
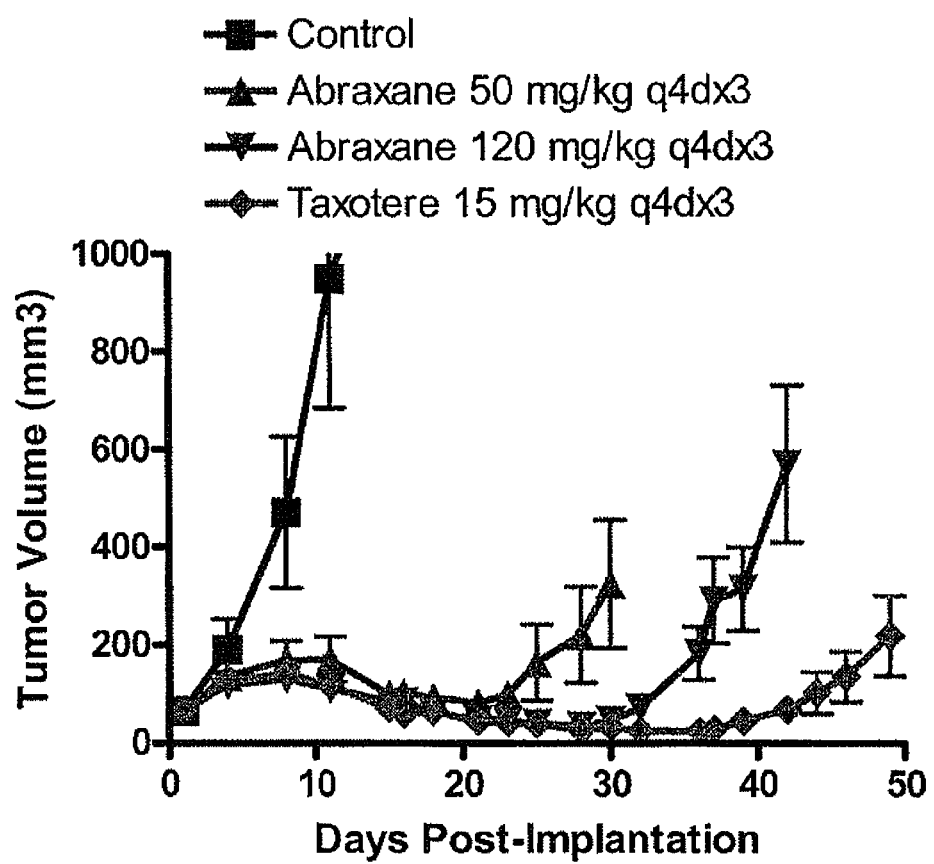
FIG. 10A-B illustrate the comparative efficacy (A, tumor volume) and toxicity (B, % weight loss) of Abraxane and Taxotere for the treatment of a MDA-MB-231 xenograft.
Figure 10B:
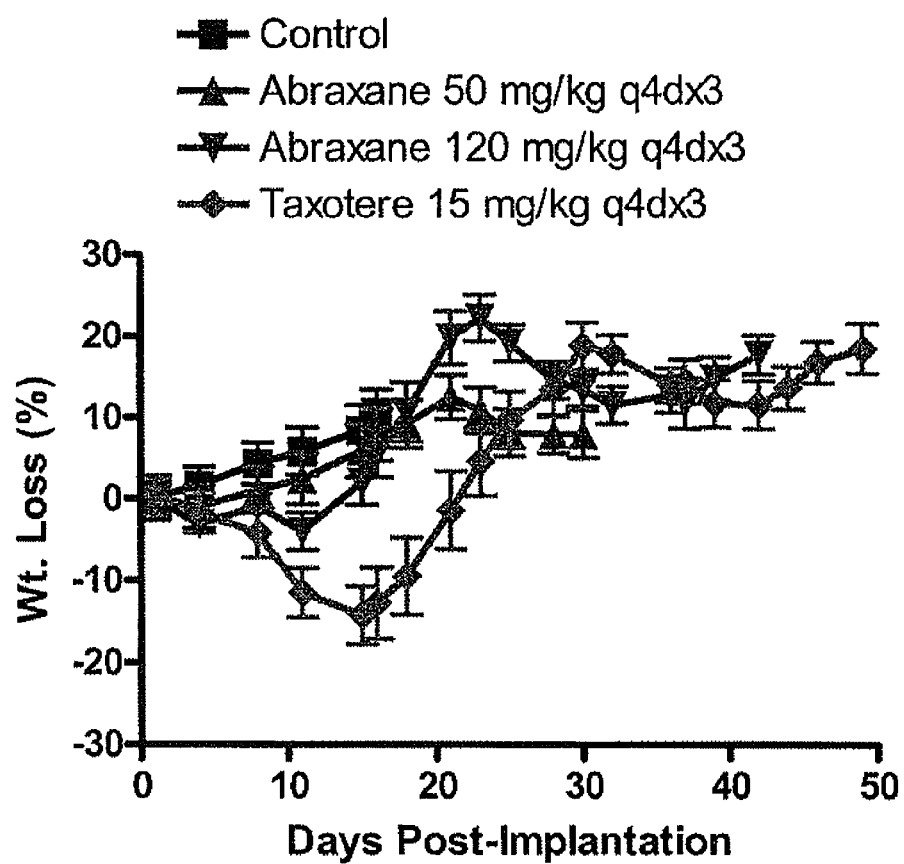

In the HT29 xenograft, ABX was more effective than TAT (15 mg/kg) at both dose levels ($p=0.0057$ for ABX 50 mg/kg and $p<0.0001$ for ABX 120 mg/kg) (see FIG. 8A). With the PC3 xenograft, ABX was less effective than TAT (15 mg/kg) at 50 mg/kg ($p<0.001$) but, equally effective as TAT (15 mg/kg) at 120 mg/kg (p=ns) (FIG. 9A) and less toxic (less weight loss, FIG. 9B). Finally, with the MDA-MB-231 xenograft, ABX was less effective than TAT (15 mg/kg) at both dose levels ($p<0.0001$ and $p<0.0001$) (see FIG. 10A).

Figure 7A:
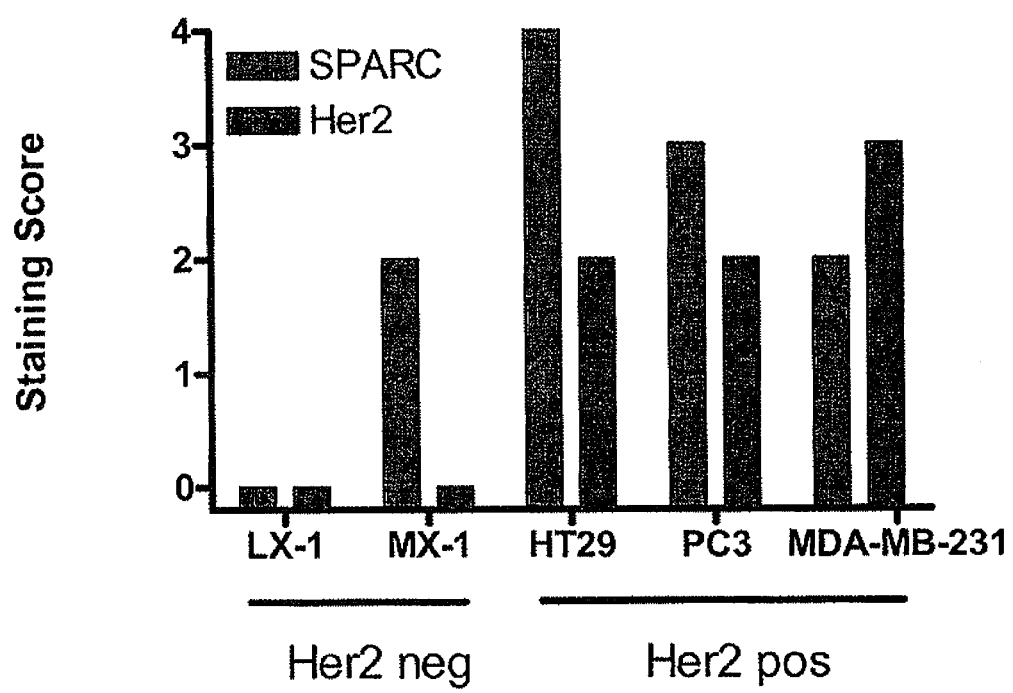
FIG. 7A-B illustrate the Her2 and SPARC status of the five tumor types (A) (SPARC, left bar and Her2, right bar in each pair) and the relative efficacy of Abraxane versus Taxotere (B).
Figure 7B:
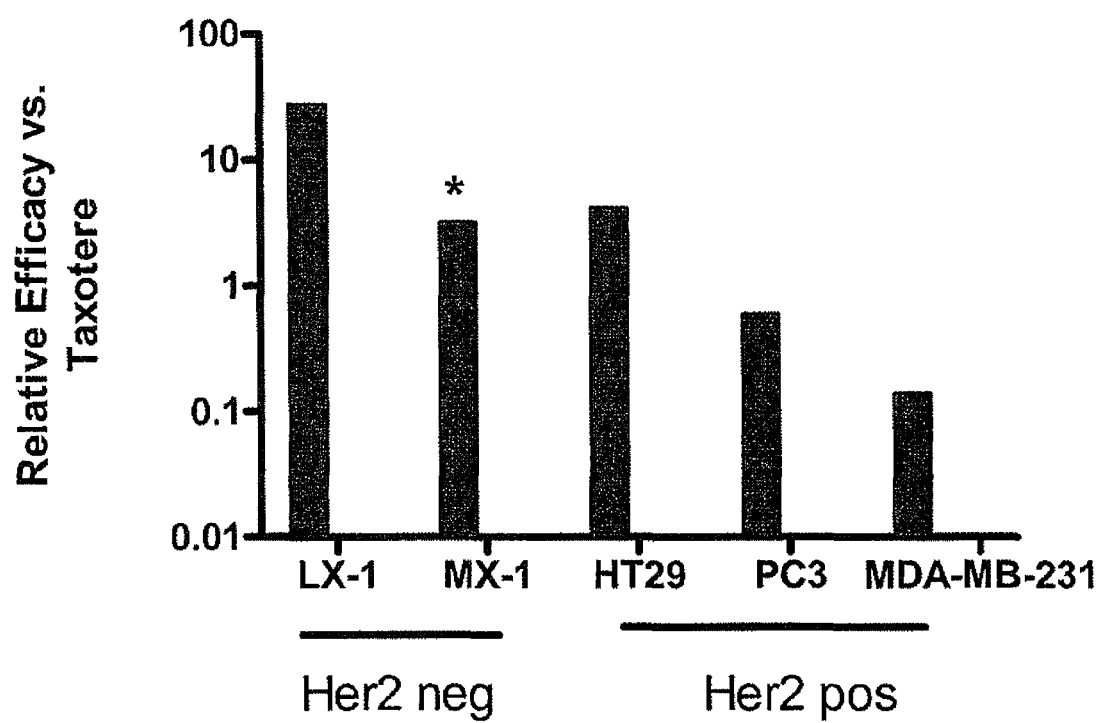

The Her2 and SPARC status of the five tumor types is shown in FIG. 7A and the relative efficacy of ABX versus TAX is shown in FIG. 7B. Relative efficacy (TAT tumor volume/ABX tumor volume) was calculated using 15 mg/kg TAT and 120 mg/kg ABX, (except for MX-1 where the relative tumor efficacy was calculated using 15 mg/kg TAX and 15 mg/kg ABX.) In the Her2-positive xenografts (HT29, PC3, and MDA-MB-231), ABX efficacy relative to TAT increased with increasing SPARC expression (see FIG. 7).

Thus, this example shows that, in the model system used, in four of five xenograft tumors tested, ABX was more effective or equally effective compared to TAT and that, in the Her2-positive xenografts tested, ABX efficacy relative to TAX is positively correlated with SPARC expression.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating a tumor of the breast, prostate or colon in a mammal with a chemotherapeutic agent or other anticancer agent comprising: (a) isolating a biological sample from the mammal, (b) detecting the expression of SPARC protein in the biological sample, (c) quantifying the amount of SPARC protein in the biological sample to determine whether the biological sample is positive for SPARC expression, (d) detecting the expression of Her2 protein in the biological sample, (e) quantifying the amount of Her2 protein in the biological sample to determine if the biological sample is positive for Her2 expression, and (f) if the biological sample is positive for SPARC expression and positive for Her2 expression, administering a therapeutically effective amount of the chemotherapeutic agent or other anticancer agent.

2. The method of claim 1, wherein the chemotherapeutic agent is select from the group consisting of docetaxel, paclitaxel, taxanes, platinum compounds, antifolates, antimetabolites, intimitotics, DNA damaging agents, proapoptotics, differentiation inducing agents, antiangiogenic agents, antibiotics, hormones, peptides, and combinations thereof.

3. The method of claim 1, wherein the chemotherapeutic agent comprises particles of protein-bound drug.

4. The method of claim 3, wherein the protein component of the protein-bound drug particles comprises albumin.

5. The method of claim 1, wherein the chemotherapeutic agent comprises particles of albumin-bound paclitaxel.

6. The method of claim 5, wherein more than 50% of the chemotherapeutic agent is in nanoparticle form.

7. The method of claim 6, wherein the paclitaxel dose is from about 30 mg/m2 to about 1000 mg/m$^2$ with a dosing cycle of about 3 weeks.

8. The method of claim 1, wherein the mammal is a human.

* * * * *